United States Patent
Shiono et al.

(10) Patent No.: US 7,510,553 B2
(45) Date of Patent: Mar. 31, 2009

(54) MEDICAL ENERGY IRRADIATING APPARATUS

(75) Inventors: Hiroshi Shiono, Tokyo (JP); Akira Sakaguchi, Kanagawa (JP); Yuichiro Irisawa, Kanagawa (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 672 days.

(21) Appl. No.: 11/090,241

(22) Filed: Mar. 28, 2005

(65) Prior Publication Data

US 2005/0222559 A1    Oct. 6, 2005

(30) Foreign Application Priority Data

Mar. 31, 2004 (JP) ............... 2004-106089

(51) Int. Cl.
A61B 18/20 (2006.01)

(52) U.S. Cl. .............. 606/11; 606/12; 606/27; 606/31

(58) Field of Classification Search ................ 600/549; 606/11–12, 27–31, 41, 42
See application file for complete search history.

(56) References Cited

U.S. PATENT DOCUMENTS

| | | | |
|---|---|---|---|
| 4,950,267 A | | 8/1990 | Ishihara et al. |
| 4,955,380 A | * | 9/1990 | Edell ............... 600/355 |
| 5,066,294 A | * | 11/1991 | Cosmescu ............ 606/11 |
| 5,292,320 A | | 3/1994 | Brown et al. |
| 5,496,308 A | | 3/1996 | Brown et al. |
| 5,620,479 A | | 4/1997 | Diederich et al. |
| 5,623,940 A | * | 4/1997 | Daikuzono ............ 600/439 |
| 5,924,997 A | * | 7/1999 | Campbell .............. 600/549 |
| 5,964,791 A | | 10/1999 | Bolmsjö |

(Continued)

FOREIGN PATENT DOCUMENTS

JP    01282801 A   *  11/1989

(Continued)

OTHER PUBLICATIONS

Search Report issued in EP 05 00 6392, Jul. 26, 2005, EPO, Munich, DE.

(Continued)

*Primary Examiner*—Michael Peffley
*Assistant Examiner*—Vincent Sica
(74) *Attorney, Agent, or Firm*—Buchanan Ingersoll & Rooney PC

(57) ABSTRACT

A temperature measuring unit of a temperature sensor has electrodes disposed on the upper and lower surfaces of a temperature measuring element, thin-film substrates disposed on the upper and lower surfaces of the electrodes, and laser beam shield plates disposed on the upper and lower surfaces of the thin-film substrates. One of the electrodes is bonded to the temperature measuring element by a conductive adhesive, and the other electrode is not bonded to the temperature measuring element by a conductive adhesive. When the temperature sensor is bonded to a hollow cylinder of an insert, the temperature measuring unit is curved along the surface of the hollow cylinder, tending to develop tensile stresses in the other electrode. At this time, the other electrode is positionally displaced depending on the developed tensile stresses, allowing the temperature sensor to be adjusted in length. Consequently, the temperature sensor is prevented from being broken or damaged.

18 Claims, 21 Drawing Sheets

U.S. PATENT DOCUMENTS

| | | |
|---|---|---|
| 6,152,951 A | 11/2000 | Hashimoto et al. |
| 6,162,184 A * | 12/2000 | Swanson et al. ............ 600/549 |
| 6,283,957 B1 | 9/2001 | Hashimoto et al. |
| 6,379,347 B1 | 4/2002 | Maki et al. |
| 6,520,959 B1 | 2/2003 | Iwahashi et al. |
| 6,544,257 B2 | 4/2003 | Nagase et al. |
| 6,562,029 B2 | 5/2003 | Maki et al. |
| 6,579,243 B2 * | 6/2003 | Kokate et al. ................ 600/549 |
| 6,579,286 B1 | 6/2003 | Maki et al. |
| 6,605,082 B2 | 8/2003 | Hareyama et al. |
| 6,695,871 B1 | 2/2004 | Maki et al. |
| 6,764,485 B2 | 7/2004 | Hareyama et al. |
| 6,817,997 B2 * | 11/2004 | Furuno et al. .................. 606/9 |

FOREIGN PATENT DOCUMENTS

| | | |
|---|---|---|
| JP | 2-304319 A | 12/1990 |
| WO | 93/04727 | 3/1993 |

OTHER PUBLICATIONS

Official Action issued in EP 05 00 6392, Aug. 22, 2008, EPO, Munich, DE.

* cited by examiner

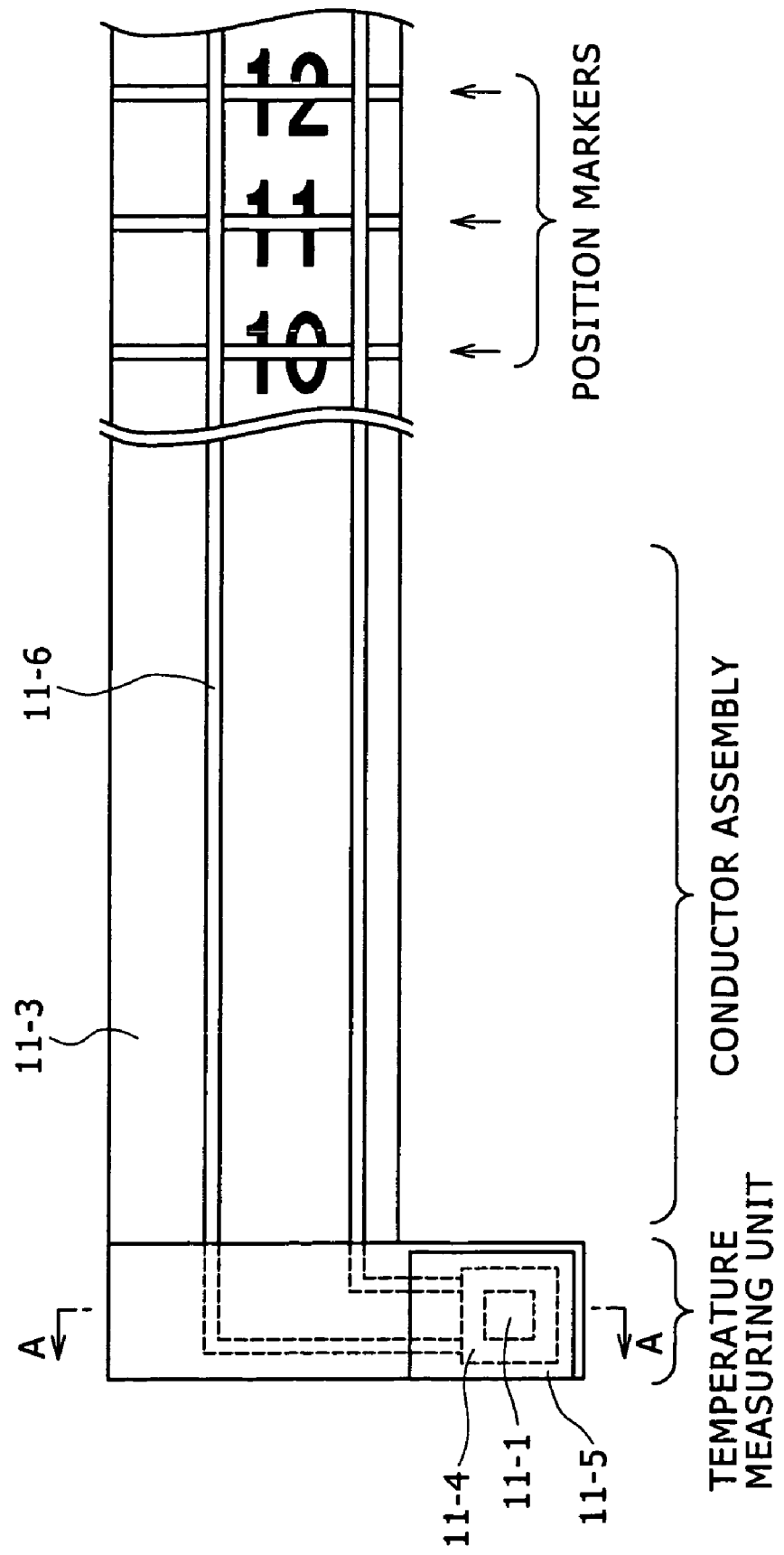

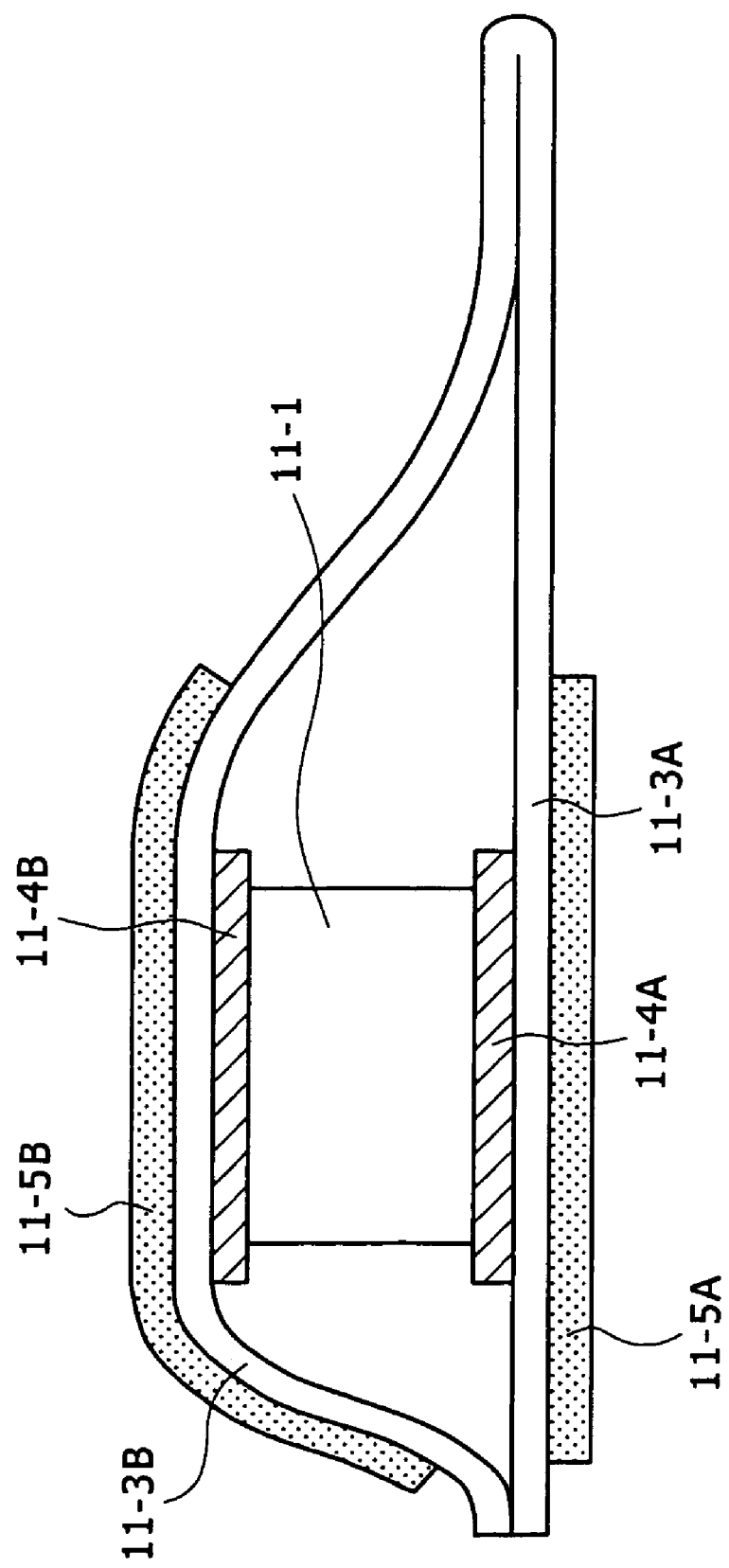

Tmax: MEASURED VALUE OF MAXIMUM TEMPERATURE OF CAVITY WALL AT LASER BEAM IRRADIATION
Tu : MEASURED VALUE OF SURFACE TEMPERATURE
Tcool: COOLANT TEMPERATURE

MEDICAL ENERGY IRRADIATING APPARATUS

BACKGROUND OF THE INVENTION

The present invention relates to a medical energy irradiating apparatus for irradiating a living tissue with energy to treat or diagnose the living tissue. More particularly, the present invention relates to a medical energy irradiating apparatus including a temperature sensor disposed in an insert portion to be inserted into a living body for accurately measuring the temperature of the living body, which it is being irradiated with an energy during treatment or diagnosis, without the need for thrusting into the living body.

There have been known in the art medical energy irradiating apparatus having an elongate insert portion to be inserted into a living body through a body cavity or a small incision. When the insert portion is inserted into the living body, the insert portion irradiates a living tissue including an affected region with an energy such as a laser beam, a microwave, a radio wave, an ultrasonic wave, or the like to thermally modify, necrose, coagulate, cauterize, or evaporate the tissue of the affected region or a surrounding tissue including the affected region.

The medical energy irradiating apparatus generally directly apply the energy to the surface layer of a living tissue or the affected region positioned closely thereto. The medical energy irradiating apparatus are also used to treat, with heat, an affected region positioned deeply in a living tissue, such as a prostatic hypertrophy, a prostatic cancer, or a prostatitis.

For example, International Publication No. WO93/04727 discloses a technique proposing a process of applying a laser beam to solidify or contract some tissue of a cancer or a prostate. According to this technique, a coolant is introduced into a balloon to prevent the surface of a urethra held in contact with the balloon from being heated, while only the cancer or the prostate located inside is being heated. However, since the laser beam is applied from a fixed laser beam irradiator, the laser beam needs to be applied at a low output level to prevent the surface of a urethra from being heated. Hence, the laser beam needs to be applied for a long period of time. International Publication No. WO93/04727 reveals a balloon catheter having a thermocouple disposed in the balloon to be located in an intermediate position in a prostatic urethra for monitoring the temperature of a urethral tissue. The thermocouple is disposed within the balloon and held out of direct contact with the urethra, and the coolant is circulated through the balloon. Therefore, the temperature measured by the thermocouple does not appear to be accurately representative of the temperature of the prostatic urethra. U.S. Pat. No. 5,964,791 discloses a process of thrusting into a prostate with a temperature sensor to accurately measure the temperature of the urethra (direct measuring process).

U.S. Pat. No. US6,579,286 discloses, as an example of heat treatment device, a laser beam irradiating apparatus for guiding a laser beam into a urethra to treat a prostatic hypertrophy. The laser beam irradiating apparatus has a laser beam irradiation portion that is continuously movable to change the direction of the applied laser beam at all times. However, since the laser beam irradiating apparatus is arranged to concentrate the laser beam on a target region, the target region is heated to a high temperature while holding a surrounding tissue around the target region at a lower temperature. Even if the target region is positioned deeply in the living tissue, therefore, any damage to the living tissue that is located between the laser beam irradiator and the target region is minimized.

A therapeutic procedure for treating a prostatic hypertrophy with the laser beam irradiating apparatus will be described below. First, the doctor inserts the insert portion of the laser beam irradiating apparatus into the urethra of the patient. The insert houses therein a laser beam irradiator having a reflecting surface for reflecting a laser beam which is generated by a laser beam generator, guided by an optical fiber, and emitted from the tip end of the optical fiber. The insert portion also houses therein an endoscope, and inlet outlet pipes for a coolant for cooling the laser beam irradiator. Then, the doctor positions the laser beam irradiator while observing the urethra with the endoscope in the insert through an observation window disposed in the insert, and then applies the laser beam to a target region in the patient.

The heat treatment device referred to above needs to measure the temperature of a treated region in order to monitor the treatment in progress. The temperature of the treated region (the target region to be irradiated with the laser beam) positioned deeply in the living body can be measured by a process of thrusting into the living tissue with a temperature sensor to directly measure the temperature of the deep region (direct measuring process) or a process of bringing a temperature sensor into contact with the surface layer of the living body near the treated region to accurately measure the temperature of the surface layer of the living body and estimating the temperature of the deep region based on the measured temperature.

Though the direct measuring process is able to accurately measure the temperature of the treated region, it is disadvantageous in that it invites side effects such as hemorrhage and infectious disease because the living body is injured by being pierced with the temperature sensor, resulting in an increased number of days that the patient needs to stay in the hospital. For this reason, there has been a demand for a technique to accurately measure the temperature of the surface of the living body while it is being treated by an energy irradiation, thereby increasing the accuracy to estimate the temperature of a deep living tissue.

Problems that arise regarding the accurate measurement of the temperature of the surface of the living body will be described below. Conventional Temperature sensors have a temperature measuring element such as a thermistor and two leads connected thereto, which are placed in a tangle-free manner in a protective tube. However, the protective tube makes the insert portion to be inserted into the living body thick, posing an increased burden on the patient. The leads that are employed tend to cause the thermistor to be installed in different positions, making it impossible to measure accurate temperatures.

It may be proposed to place the temperature measuring element and the leads within the insert portion. If the temperature measuring element is placed in the insert portion of an energy treatment device where a coolant is circulated in the insert portion for cooling an energy emission unit and the living body contacted by the insert portion, then the coolant affects the temperature measuring element. Consequently, there has been desired a temperature sensor less susceptible to the coolant and is yet capable of accurately measuring the surface temperature of a living body.

One solution would be to attach the temperature measuring element and the leads to the outer surface of the insert. However, this approach needs to meet the following requirements:

1. The temperature measuring element will not be affected by the coolant.

2. The temperature measuring element will be installed easily and accurately in a desired position.

3. When the temperature measuring element and the leads are attached, the leads will not be damaged and will keep electrically connected to the temperature measuring element.

4. The insert portion will not have protrusions on its surface, which would otherwise be liable to damage the living body when the insert portion is inserted into the living body.

5. The temperature measuring element will not be directly affected by the energy that is applied to the living body.

SUMMARY OF THE INVENTION

It is therefore an object of the present invention to provide a medical energy irradiating apparatus of a structure that is simple and inexpensive to manufacture and capable of accurately measuring the temperature of a living tissue when the doctor treats a prostatic hypertrophy or a prostatic cancer with heat, using the medical energy irradiating apparatus.

To achieve the above object, a medical energy irradiating apparatus includes an insert portion for being inserted into a living body, a temperature sensor disposed on the insert portion, and an energy irradiating for applying an energy to a living tissue of the living body. The temperature sensor includes a single flexible thin-film substrate, at least first and second conductors disposed on the thin-film substrate, and a temperature measuring unit. The temperature measuring unit is disposed on the insert portion.

Preferably, the temperature measuring unit includes substantially plate-like first and second electrodes disposed on the thin-film substrate and electrically coupled respectively to the first and second conductors, and a substantially plate-like temperature measuring element. The first and second electrodes are electrically coupled to the temperature measuring element.

Preferably, the temperature measuring element has a first surface disposed on the first electrode, the first electrode being fixed and electrically coupled to the temperature measuring element, and wherein the temperature measuring element has a second surface opposite to the first surface, the second electrode being disposed on the second surface, the second electrode being electrically coupled to the temperature measuring element.

Preferably, the single flexible thin-film substrate is curved to dispose the second electrode on a second surface opposite to a first surface of the temperature measuring element.

Preferably, the thin-film substrate is disposed along a longitudinal direction on an outer surface of the insert portion.

Preferably, the medical energy irradiating apparatus further includes a covering tube covering a portion of an outer surface of the insert portion and thermally shrunk over the insert portion and the temperature sensor to press the temperature measuring element and the second electrode against each other.

Preferably, the temperature sensor further includes a thin metal film shielding the temperature measuring element against light.

Preferably, the thin metal film is disposed on the thin-film substrate, and the thin-film substrate with the metal film disposed thereon is folded to cover the temperature measuring element.

Preferably, the medical energy irradiating apparatus further includes an energy irradiating window for applying an energy therethrough to a living tissue of the living body. The temperature measuring unit being disposed on said energy irradiating window.

Preferably, the insert portion includes a hollow cylinder, the hollow cylinder having an opening defined in a side wall thereof and serving as the energy irradiating window.

Preferably, the medical energy irradiating apparatus further includes an optically transparent glass applied to the hollow cylinder in covering relation to the opening.

Preferably, the medical energy irradiating apparatus further includes an optically transparent synthetic resin film applied to the hollow cylinder in covering relation to the opening.

Preferably, the optically transparent synthetic resin film prepares scale, which is for operator to measure tissue surface.

Preferably, the medical energy irradiating apparatus further includes at least an outer tube covering the opening portion.

Preferably, the thin-film substrate has depth markers for the user to read a length by which the insert portion is inserted into the living body.

Preferably, the temperature sensor further includes maximum surface temperature estimating means for estimating a maximum temperature of a surface of the living tissue, which is irradiated with the energy, based on a temperature measured by the temperature sensor.

Preferably, the temperature sensor further includes deep region temperature estimating means for estimating a deep region temperature in the living tissue, which is irradiated with the energy, based on a temperature measured by the temperature sensor.

Preferably, the temperature sensor further includes control means for controlling the energy applied to the living tissue based on a temperature measured by the temperature sensor.

Preferably, the energy includes laser.

Preferably, the medical energy irradiating apparatus further includes irradiating means disposed in the insert and having a reflecting surface for reflecting the laser beam through the energy irradiating window to the living tissue, moving means for reciprocating moving the irradiating means in a longitudinal direction of the insert, angle changing means for changing an angle through which the energy is applied to the living tissue by the irradiating means, and decision means for determining whether the irradiating means is correctly controlled to move reciprocating by the moving means based on a temperature measured by the temperature sensor.

According the present invention, there is also provided a medical energy irradiating apparatus including an insert for being inserted into a living body, an energy irradiating window defined in a side wall of the insert for applying a generated energy therethrough to a living tissue of the living body, and a plurality of temperature sensors disposed in respective different positions on an outer surface of the insert. Each of the temperature sensors includes a single flexible thin-film substrate, at least first and second conductors disposed on the thin-film substrate, and a temperature measuring unit.

The medical energy irradiating apparatus according to the present invention is capable of accurately measuring the temperature of a living tissue as it is treated with heat, though the medical energy irradiating apparatus is simple in structure and inexpensive to manufacture. Therefore, the doctor who operates the medical energy irradiating apparatus can correctly monitor the temperature of the living tissue as it is treated with heat to cure a prostatic hypertrophy, for example, and hence can treat the living tissue with greater safety.

BRIEF DESCRIPTION OF THE DRAWINGS

These and other objects of the invention will be seen by reference to the description, taken in connection with the accompanying drawing, in which:

FIG. 7A is a front elevational view showing a structure of the temperature sensor;

FIG. 7B is a cross-sectional view taken along line A-A of FIG. 7A;

DETAILED DESCRIPTION OF THE PREFERRED EMBODIMENTS

The present invention will be described below as being applied to a medical energy irradiating apparatus for treating, with heat, a prostatic hypertrophy. However, the principles of the present invention are not limited to such a medical energy irradiating apparatus for treating, with heat, a prostatic hypertrophy. A laser beam will be described as an example of energy used for treating, with heat, a prostatic hypertrophy. However, the energy is not limited to a laser beam, but an electromagnetic wave such as a microwave, a radio wave, or the like, or an elastic wave such as an ultrasonic wave, a sound wave, or the like may be used as the energy.

The laser beam that can be used may include a divergent beam, a parallel beam, or a convergent beam. An optical system for converting a laser beam into a convergent beam may be disposed in the path of the laser beam. Though the laser beam is not limited to any particular laser beams insofar as they can reach a deep region in a living body, the laser beam should preferably have a wavelength ranging from 500 to 2600 nm, more preferably from 750 to 1300 nm or from 1600 to 1800 nm. The laser beam may be generated by a gas laser such as an He—Ne laser or the like, a solid-state laser such as an Nd-YAG laser or the like, or a semiconductor laser such as a GaAlAs laser or the like.

[Medical Energy Irradiating Apparatus (FIG. 1)]

Figure 1:
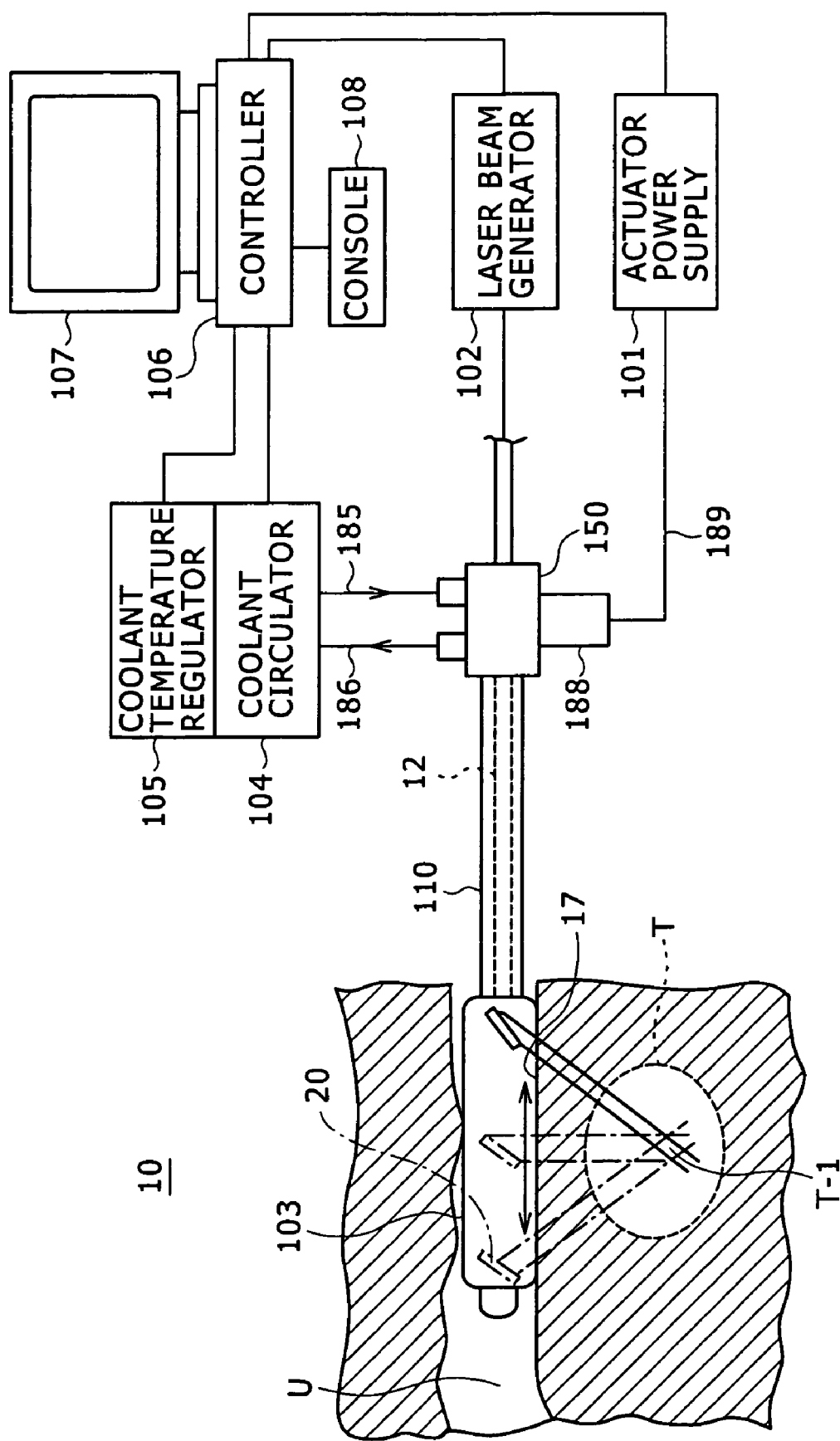
FIG. 1 is a view, partly in block form, of a system arrangement of a medical energy irradiating apparatus according to an embodiment of the present invention.

FIG. 1 shows, partly in block form, of a system arrangement of a medical energy irradiating apparatus 10 according to an embodiment of the present invention.

As shown in FIG. 1, the medical energy irradiating apparatus 10 is a lateral-emission laser beam irradiating apparatus, and includes an applicator 110 having an insert portion 103 to be inserted into a body cavity U such as an urethra, for example. The insert portion 103 is mounted on the distal end of the applicator 110, and an outside diameter of the insert portion 103 is not limited to any values insofar as it can be inserted into the body cavity U. However, the outside diameter of the insert portion 103 should preferably be in the range from 2 to 20 mm, and more preferably in the range from 3 to 8 mm.

The insert portion 103 houses therein a laser beam irradiation portion 20 that is reciprocating movable in the longitudinal direction of the insert portion 103. A laser beam is guided by an optical fiber 12 extending through the applicator 110 and emitted from the distal end of the optical fiber 12. The laser beam emitted from the optical fiber 12 is reflected by the laser beam irradiation portion 20 and applied through a laser beam irradiating window defined in a side wall of the insert portion 103 to a target region T-1 to be irradiated in a living tissue T.

The laser beam irradiation portion 20 is coupled through a reciprocating movable member 23 (see FIG. 2) to a drive unit 150 disposed on the proximal end of the applicator 110. When the reciprocating movable member 23 is moved in the longitudinal direction of the insert portion 103 by the drive unit 150, the laser beam irradiation portion 20 is reciprocating moved in the directions indicated by the arrows.

The drive unit 150 has a cam mechanism (not shown) for converting rotary motion of a motor 188 into reciprocating motion. Therefore, when the motor 188 is energized, its rotary motion is converted by the cam mechanism into reciprocating motion that is transmitted to the reciprocating movable member 23, which moves the laser beam irradiation portion 20 in the longitudinal direction of the insert portion 103.

The applicator 110 has a plurality of lumens (not shown) defined longitudinally therein and communicating with the insert portion 103 for circulating a coolant. The lumens are connected respectively to a coolant supply tube 185 and a coolant return tube 186 which extend from a coolant circulator 104. The coolant is supplied through the coolant supply tube 185 to the insert portion 103 to cool the laser beam irradiation portion 20 for thereby preventing the laser beam irradiation portion 20 from being overheated, and also to cool the surface of the body cavity U, which is held in contact with the insert portion 103 through the wall of the insert portion 103, for thereby preventing a correct body tissue, which is heated by the applied laser beam, from being damaged.

The coolant circulator 104 supplies the coolant at a preset rate through the applicator 110 to the insert portion 103 based on a control signal from a controller 106. A coolant temperature regulator 105 that is coupled to the coolant circulator 104 heats or cools the coolant in the coolant circulator 104 to regulate the temperature of the coolant based on a control signal from a controller 106. The motor 188 is energized to rotate a preset rotational speed based on a control signal from a controller 106.

The controller 106 has a console 108 serving as an input unit, a display 107 for displaying input information and apparatus information, a control unit (not shown) for controlling various parts of the controller 106, a memory (not shown) for storing various items of information, and an input/output unit (not shown) for inputting and outputting various items of information.

The coolant is supplied from the coolant circulator 104 through the coolant supply tube 185 to the insert portion 103, the motor 188 is rotated, and a laser beam generator 102 is operated to treat, with heat, a prostatic target region T-1 (target point) to be irradiated with a laser beam.

A laser beam generated by the laser beam generator 102 is transmitted through the optical fiber 12 to the laser beam irradiation portion 20 in the insert portion 103, which reflects the laser beam through the laser beam irradiating window to the target region T-1. At this time, the laser beam irradiation portion 20 is reciprocating moved axially in the insert portion 103 in periodic cycles at a frequency ranging from 2 to 10 Hz, preferably 3 to 9 Hz, periodically changing the angle of irradiation. Since all the paths along which the reflected laser beam travels cross the target region T-1 at all times, the target region T-1 is continuously irradiated with the laser beam and generates a large amount of heat. Therefore, the target region T-1 is kept at a high temperature and can effectively be treated with heat. On the other hand, the surface layer of the body cavity U is intermittently irradiated with the laser beam, generating a small amount of heat, and is cooled by the coolant supplied to the insert portion 103. Consequently, the surface layer of the body cavity U is protected from and hence is not susceptible to the heat of the laser beam.

[Insert Portion (FIGS. 2, 3, and 4)]

Figure 2:
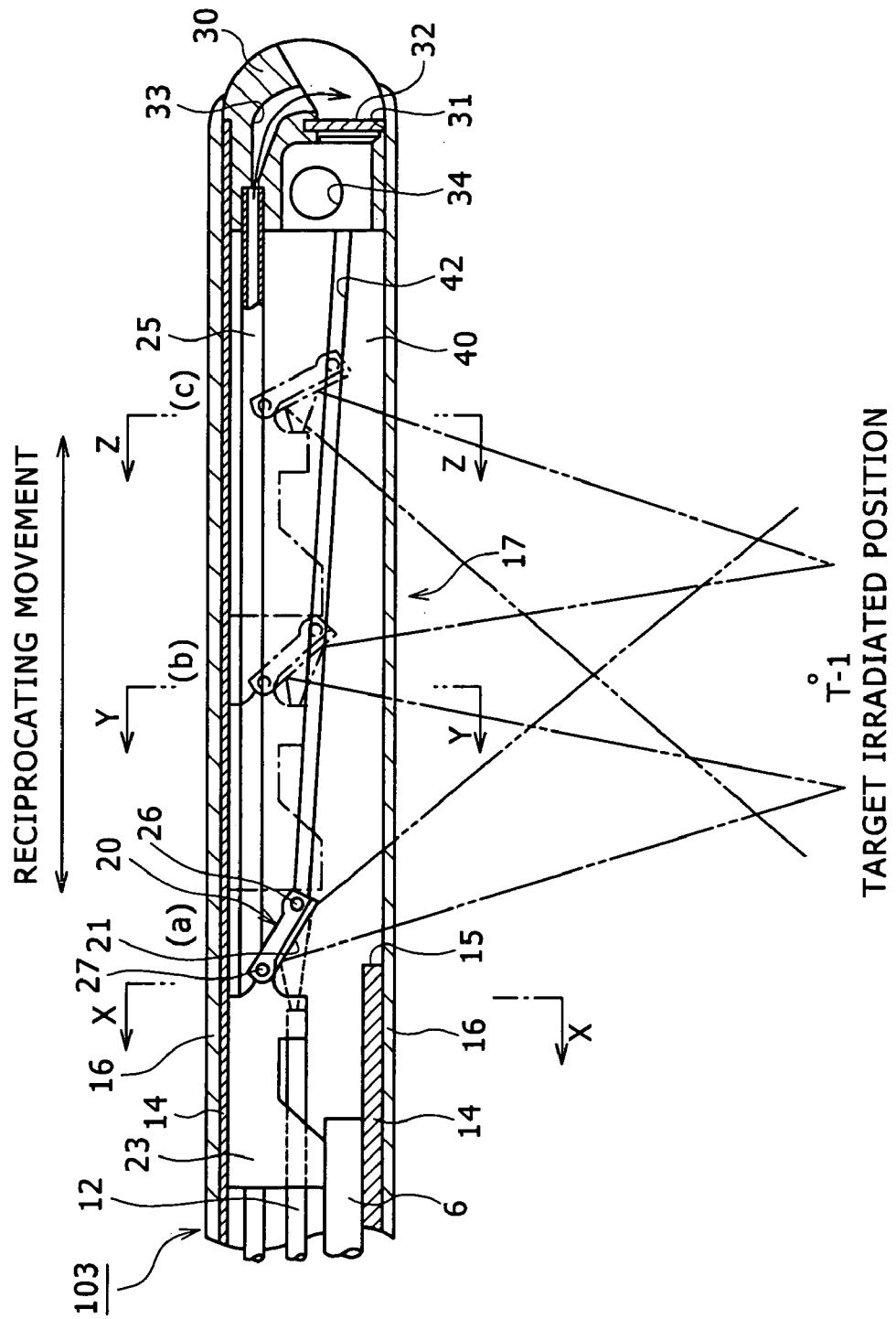
FIG. 2 is a cross-sectional view of an insert of the medical energy irradiating apparatus.
Figure 3:
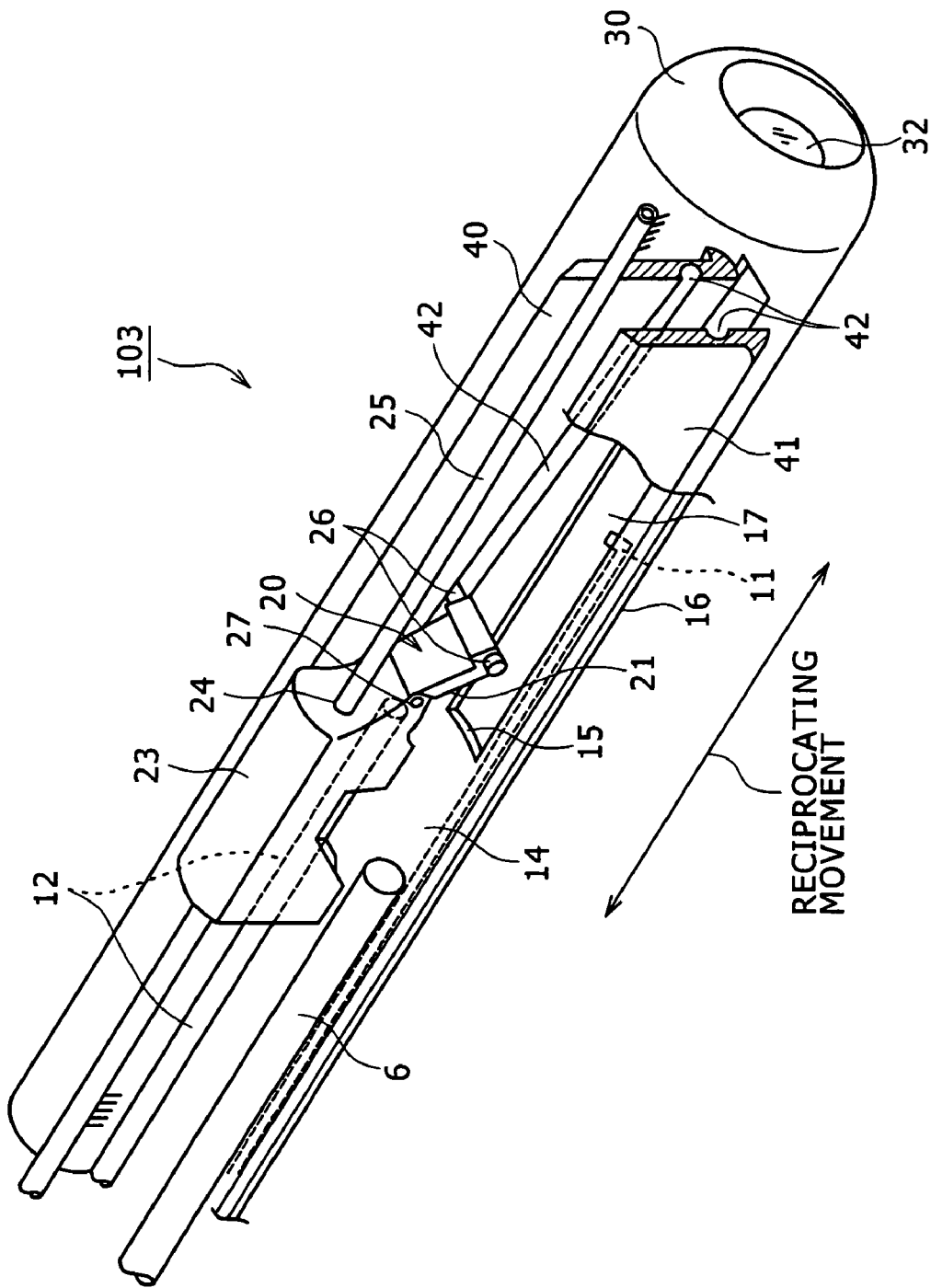
FIG. 3 is a perspective view showing an internal structure of the insert.
Figure 4:
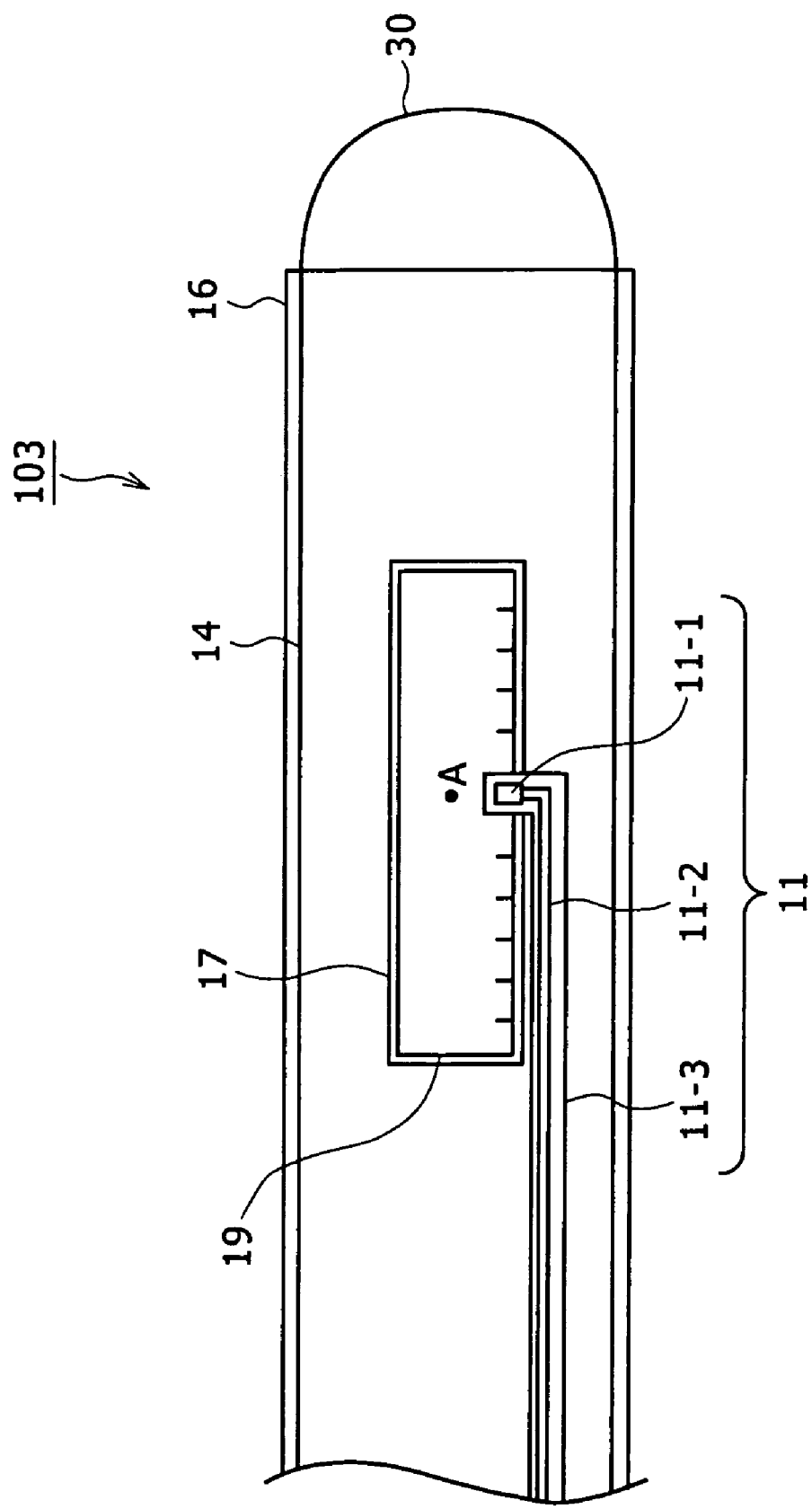
FIG. 4 is an elevational view of a temperature sensor disposed on a hollow cylinder.

The insert portion 103 will be described in greater detail below. FIG. 2 shows the insert portion 103 in longitudinal cross section, FIG. 3 shows an internal structure of the insert portion 103, and FIG. 4 shows a temperature sensor disposed on a hollow cylinder 14.

The insert portion 103 includes an elongate hollow cylinder 14 made of a hard pipe material such as stainless steel or the like, with an opening 15 defined in a side wall of the hollow cylinder 14. A graduated window seal is applied over the opening protion 15, providing a laser beam irradiating window 17. A temperature sensor 11 is mounted on the hollow cylinder 14. As shown in FIGS. 7A and 7B, the temperature sensor 11 includes a temperature measuring unit mounted on a thin-film substrate 11-3 and including a temperature measuring element 11-1 and electrodes 11-4A, 11-4B, and a conductor assembly mounted on the thin-film substrate 11-3 and including conductors 11-6. The hollow cylinder 14 has its outer circumferential surface covered entirely or partly with an outer tube 16, which is highly permeable to the laser beam. A cap 30 is sealingly fixed to the distal end of the hollow cylinder 14. The cap 30 has an optically transparent front window 32 for observing a forward region when the insert portion 103 is inserted into the body cavity U.

The insert portion 103 houses therein a pair of walls 40, 41 spaced laterally from each other, defining an inner space therebetween in the insert portion 103. The insert portion 103 also houses therein the laser beam irradiation portion 20 with the reflecting surface 21, the reciprocating movable member 23, a monorail pipe 25, nonparallel grooves 42, an endoscope 6, and coolant lumens. The reciprocating movable member 23 supports the laser beam irradiation portion 20. The monorail pipe 25 has the reciprocating movable member 23, which is reciprocating movable in the longitudinal direction of the insert portion 103. The nonparallel grooves 42 are defined in the respective walls 40, 41 for changing the angle of the laser beam irradiation portion 20 so that the laser beam reflected by the laser beam irradiation portion 20 is applied to the target region at all times. The endoscope 6 observes the living tissue. The laser beam irradiation portion 20 is rotatably supported on a pair of pivots 27 fixed to respective left and right sides of the reciprocating movable member 23 that is fixed to the distal end of the optical fiber 12. The laser beam irradiation portion 20 has a pair of lugs 26 mounted on respective left and right sides thereof and slidably fitted respectively in the nonparallel grooves 42 defined in the walls 40, 41. The nonparallel grooves 42 extend out of parallel with the longitudinal axis of the insert portion 103.

Major components of the insert portion 103 will be described below.

[Laser Beam Irradiating Window (FIGS. 5 and 6)]

Figure 5:
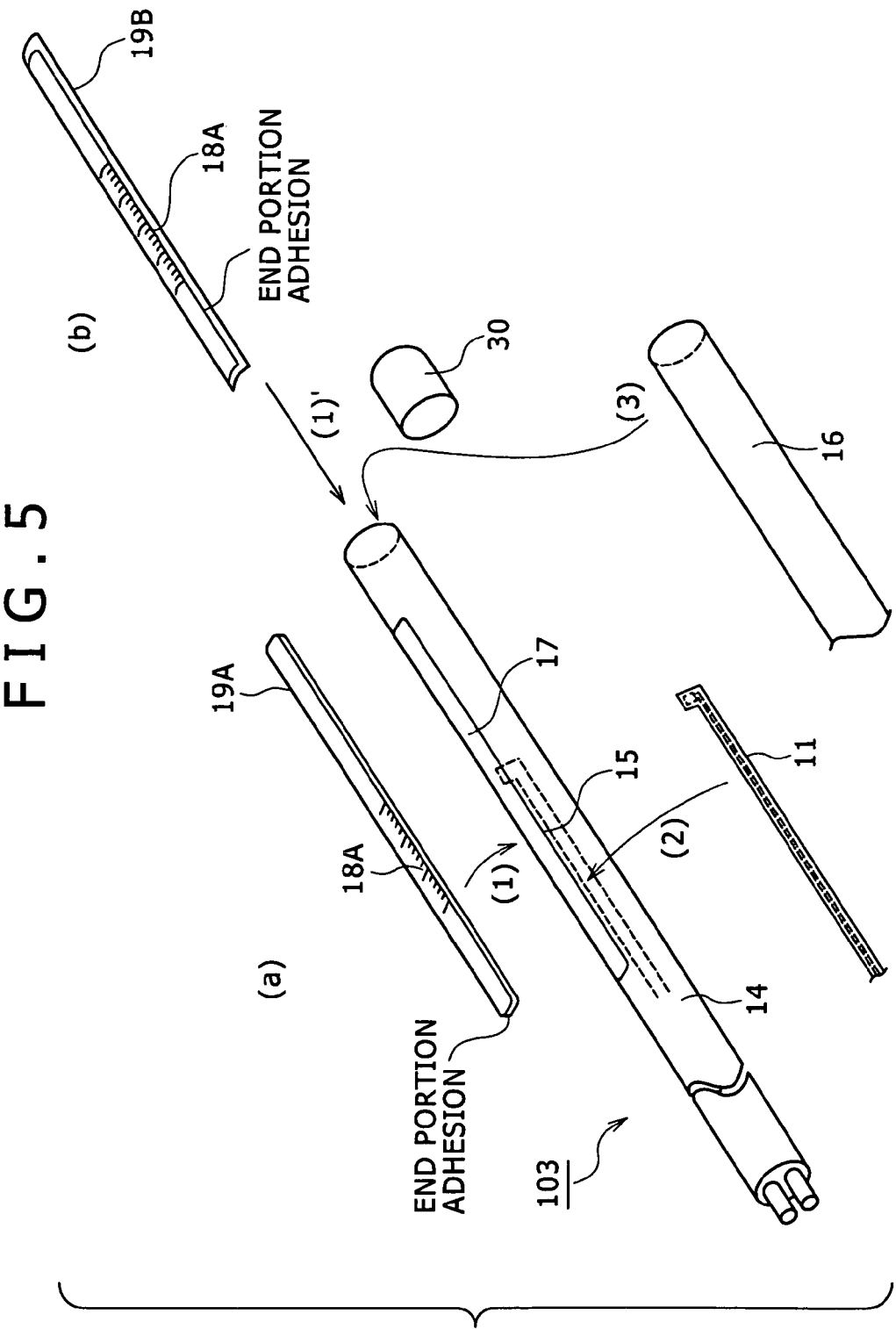
FIG. 5 is a fragmentary exploded perspective view illustrative of a process of forming a laser beam irradiating window using a graduated glass strip and then placing a temperature sensor on a hollow cylinder.
Figure 6:
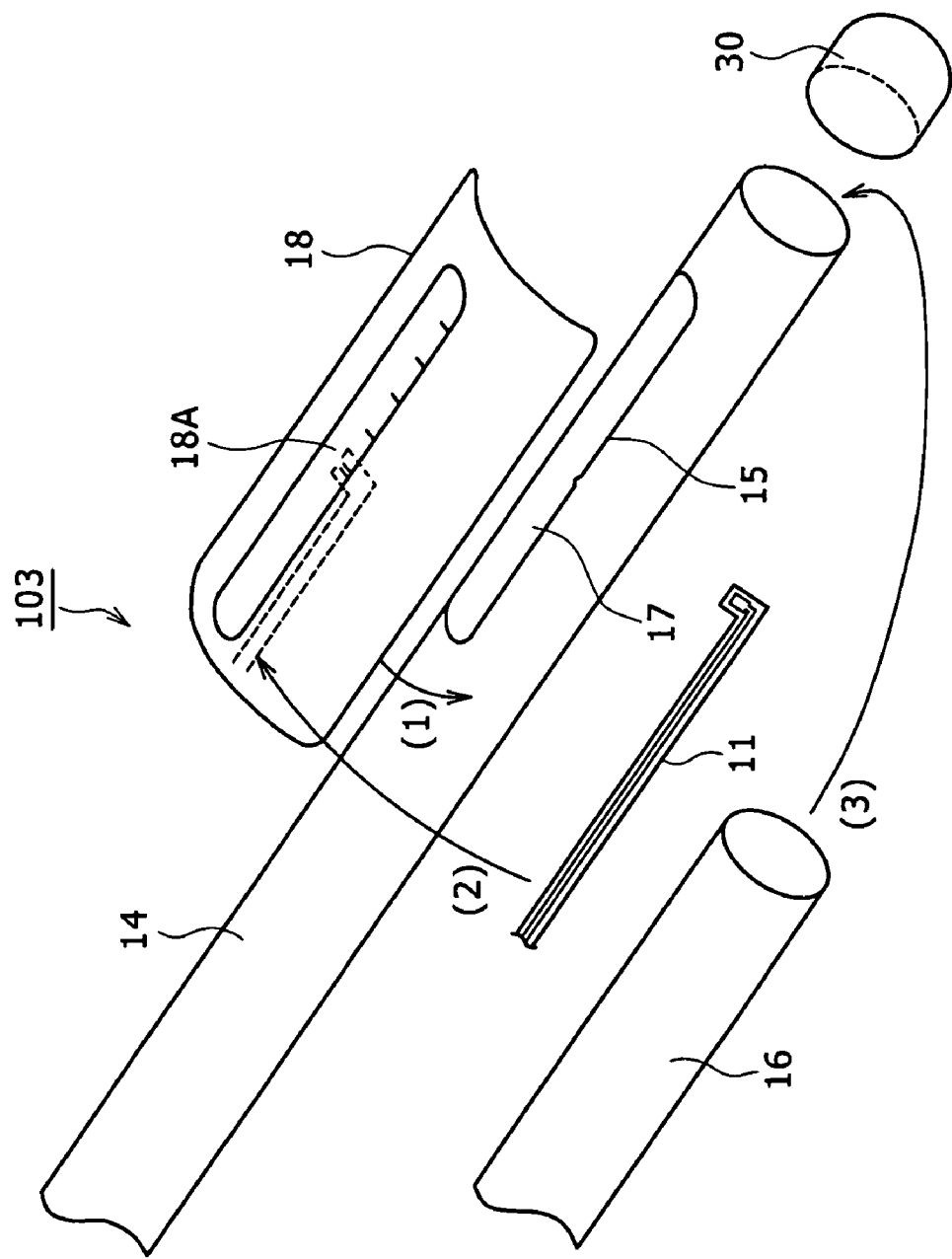
FIG. 6 is a fragmentary exploded perspective view illustrative of a process of forming a laser beam irradiating window using a graduated window seal and then placing a temperature sensor on a hollow cylinder.

FIGS. 5 and 6 are illustrative of a process of forming the laser beam irradiating window 17 using graduated glass strips 19A, 19B or a graduated window seal 18 and then placing the temperature sensor 11 on the hollow cylinder 14.

The graduated glass strip 19A or 19B is produced by pressing a thin glass sheet into an arcuately curved glass strip with heat, and making scale (graduation) 18A on the surface of the arcuately curved glass strip. The scale 18A is used to determine a position to be irradiated with a laser beam. The scale 18A is formed by printing or the like, at a position not obstructing the path of the laser beam and in a color that is not liable to absorb the laser beam.

The glass with scale (graduation) strip 19A or 19B is fixed in position over the opening 15. An adhesive is applied to an end of the glass with scale strip 19A, and the glass with scale strip 19A is fitted into the opening 15 from above and bonded to the hollow cylinder 14, as indicated at (1) in (a) of FIG. 5. Alternatively, an adhesive is applied to an end of the glass with scale strip 19B and the glass with scale strip 19B is inserted axially into the hollow cylinder 14, as indicated at (1)' in (b) of FIG. 5, after which the glass with scale strip 19B is fitted into the opening 15 within the hollow cylinder 14 and bonded to the hollow cylinder 14.

The temperature sensor 11 is fixed in the position shown in FIG. 4. The thin-film substrate 11-3, which is coated with an adhesive, is bonded to the hollow cylinder 14 in a predetermined position, and then the outer tube 16 is placed over the hollow cylinder 14, as indicated at (3) in (a) of FIG. 5. Then, the outer tube 16 is thermally shrunk to press the temperature sensor 11 in position.

The opening 15 is sealed with the window seal with scale 18. The window seal with scale 18, which is coated with an adhesive on its reverse side, is applied and bonded from above to the hollow cylinder 14 over the opening 15, as shown in FIG. 6. The window seal with scale 18 should preferably be made of a synthetic resin film with a smooth surface, e.g., a film of polyester, polycarbonate, polyethylene terephthalate (PET), or the like, which is colorless, transparent, and permeable to a laser beam. Particularly, a PET film is preferable as the material of the graduated window seal 18. The adhesive used may be any of various adhesives insofar as they can firmly bond the graduated window seal 18 to the hollow cylinder 14 to prevent the coolant circulating in the hollow cylinder 14 from leaking out of the laser beam irradiating window 17. The temperature sensor 11 is fixed such that the thin-film substrate 11-3, which is coated with an adhesive, is bonded to the hollow cylinder 14 in a predetermined position, the outer tube 16 is placed over the hollow cylinder 14 as indicated at (3) in FIG. 6, and then the outer tube 16 is thermally shrunk to press the temperature sensor 11 in position.

[Structure of the Temperature Sensor (FIGS. 7A through 7C)]

FIG. 7A is a front elevational view showing a structure of the temperature sensor, and FIG. 7B is a cross-sectional view taken along line A-A of FIG. 7A. Structural details and features of the temperature sensor 11 will be described below with reference to FIGS. 7A and 7B.

As shown in FIG. 7A, the temperature sensor 11 is constructed of the temperature measuring unit and the conductor assembly. The conductor assembly includes the thin-film substrate 11-3 and the two conductors 11-6. The thin-film substrate 11-3 is made of an insulating material such as polyimide, nylon, polyethylene, PET, or the like. The two conductors 11-6 are mounted on the thin-film substrate 11-3 and each in the form of a strip of a conductive material. The thin-film substrate 11-3 has a plurality of position (depth) markers printed thereon for the user to easily read the length of the temperature sensor 11, which has been inserted into a living body. The thin-film substrate 11-3 includes a thin film having a thickness in the range from 10 to 40 μm, preferably from 15 to 25 μm, and can flexibly be bent. As shown in FIG. 7B, the temperature measuring unit has the temperature measuring element 11-1, such as a thermistor, disposed centrally therein, and the electrodes 11-4B, 11-4A mounted respectively on the upper and lower surfaces of the temperature measuring element 11-1. Thin-film substrates 11-3B, 11-3A are disposed respectively on the upper and lower surfaces of the electrodes 11-4B, 11-4A. Laser beam shield plates 11-5B, 11-5A are disposed respectively on the upper and lower surfaces of the thin-film substrates 11-3B, 11-3A.

[First Feature of the Temperature Sensor (thickness)]

According to a first feature of the temperature sensor 11, the temperature measuring element 11-1 includes a thin thermistor to make the temperature sensor 11 as thin as possible. The temperature measuring element 11-1 is in the form of a rectangular parallelepiped and has upper and lower surfaces serving as electrically coupling surfaces. The temperature measuring element 11-1 can have its temperature accurately measured by measuring the electric resistance between the upper and lower surfaces thereof. The upper and lower surfaces of the temperature measuring element 11-1 are held in contact with the electrodes 11-4B, 11-4A, which are in the form of flat plates. For example, the components of the temperature sensor 11 have thicknesses as follows: The thickness of the thin-film substrate 11-3 is in the range from 10 to 20 μm. The thickness of the conductors 11-6 is in the range from 10 to 20 μm. The thickness of the thin-film substrate 11-4 is in the range from 10 to 20 μm. The thickness of the temperature measuring element 11-1 is about 150 μm. The thickness of the laser beam shield plates 11-5A, 11-5B is in the range from 5 to 10 μm. Therefore, the thickness of the temperature sensor 11, i.e., the thickness of the temperature measuring unit, is about 200 μm.

Figure 7C:
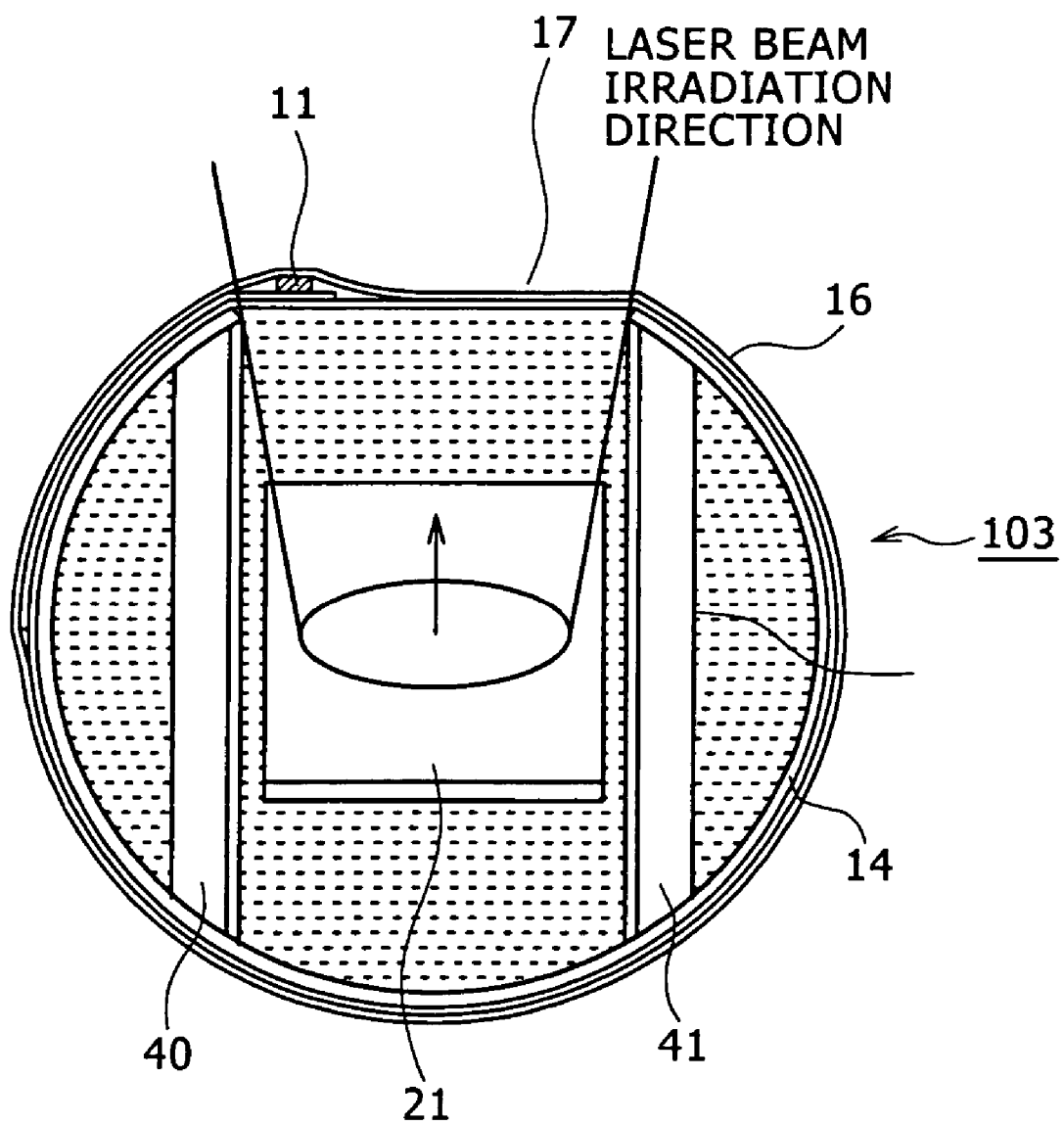
FIG. 7C is a transverse cross-sectional view showing the temperature sensor placed on the hollow cylinder.

FIG. 7C shows the temperature sensor 11 mounted on the hollow cylinder 14 at an end of the outer surface of the laser beam irradiating window 17 and fixed in position by the outer tube 16. In FIG. 7C, the hollow cylinder 14 has an outside diameter of 7 mm, the temperature sensor 11 has a thickness of 200 μm, and the outer tube 16 has a thickness of 20 μm. As can be seen from FIG. 7C, since the temperature sensor 11 is thin, the temperature sensor 11 mounted on the outer surface of the laser beam irradiating window 17 keeps the outside diameter of the insert portion 103 essentially identical to the outside diameter of the hollow cylinder 14. Therefore, when the insert portion 103 with the temperature sensor 11 installed thereon is inserted into a living body, the possibility that the temperature sensor 11 will damage the surface of the living body is reduced to the point where it will be damaged by the insert portion 103, which is free of the temperature sensor 11. Since the temperature sensor 11 is fixed in position by the outer tube 16, the temperature sensor 11 is prevented from being positionally displaced when it is in use.

In FIG. 7C, the laser beam irradiating window 17 is shown as being flat. However, the laser beam irradiating window 17 may be of an arcuately curved cross section matching the circular cross section of the hollow cylinder 14 and the temperature sensor 11 is mounted on the outer surface of the laser beam irradiating window 17. Even in that case, the possibility that the temperature sensor 11 will damage the surface of the living body is reduced to the point where it will be damaged by the insert portion 103 that is free of the temperature sensor 11. This is because the thickness of the temperature sensor 11 is reduced to about 200 μm.

[Second Feature of the Temperature Sensor (pressing electrode: FIGS. 8A through 8D)]

Figure 8A:
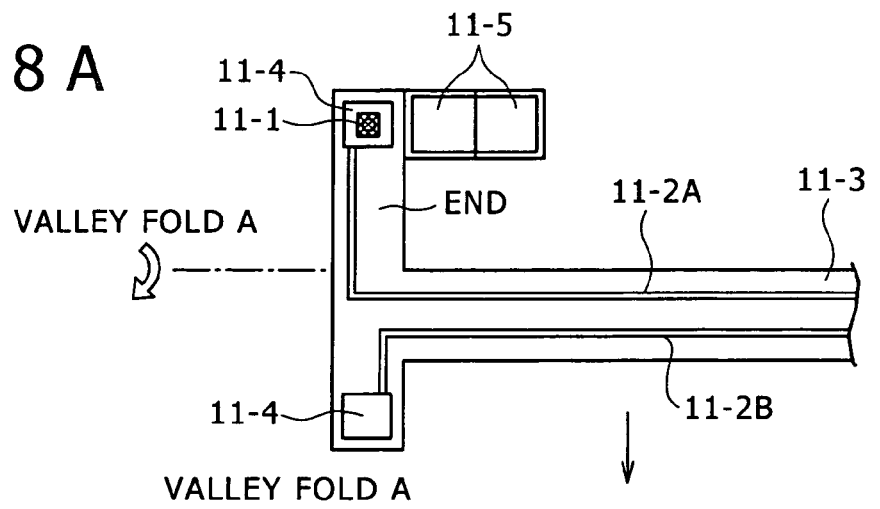
FIGS. 8A through 8D are views illustrative of a process of manufacturing the temperature sensor.

A pressing electrode according to a second feature of the temperature sensor 11 will be described below. Prior to describing the pressing electrode, a process of assembling the temperature measuring unit of the temperature sensor 11 will first be described below with reference to FIGS. 8A through 8D. FIG. 8A shows one. example of the previous state assembled into the temperature sensor 11. The temperature sensor includes conductors 11-2A, 11-2B, electrodes 11-4A, 11-4B, and a laser beam shield film 11-5, which are formed by etching or the like on a thin-film substrate 11-3 shaped as shown in FIG. 8A. The conductors 11-2A, 11-2B, the electrodes 11-4A, 11-4B, and the laser beam shield film 11-5 are formed of one conductive material, e.g., copper, on the thin-film substrate 11-3 by etching or the like. A temperature measuring element 11-1 is bonded to the electrode 11-4A by a conductive adhesive. The electrodes 11-4A, 11-4B and, the surface of the laser beam shield film 11-5 may be covered with evaporated gold. The conductors 11-2A, 11-2B need to be covered with a printed resist layer or another cover layer such as of polyimide, nylon, polyethylene, PET, or the like so as to prevent a short circuit therebetween.

Figure 8B:
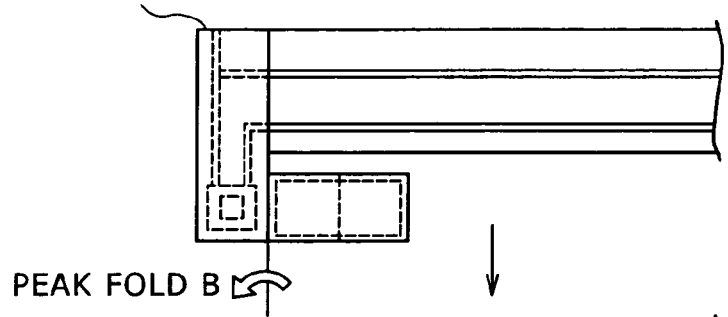
Figure 8C:
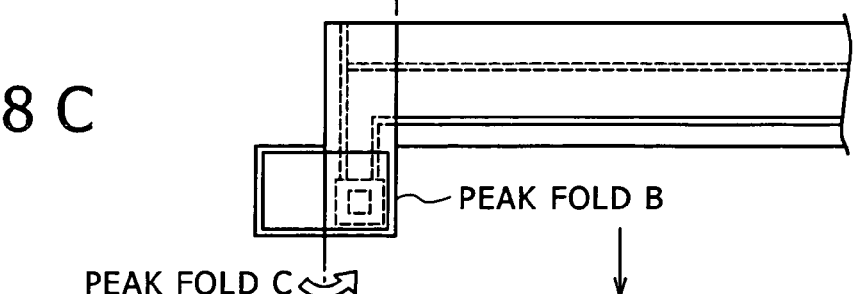
Figure 8D:
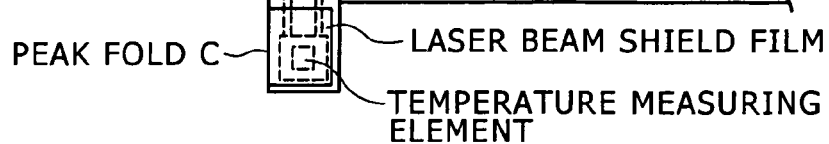

The temperature sensor 11 is assembled as shown in FIG. 8D. First, the thin-film substrate 11-3 is folded over on itself along a fold A shown in FIG. 8A. The electrode 11-4A is superimposed on the temperature measuring element 11-1 as shown in FIG. 8B. Then, the laser beam shield film 11-5 is folded over onto the electrode 11-4A along a fold B shown in FIG. 8B, as shown in FIG. 8C. Thereafter, the laser beam shield film 11-5 is folded over on itself along a fold C shown in FIG. 8C, and the laser beam shield film 11-5 is superimposed on the electrode 11-4B, as shown in FIG. 8D. Now, the temperature sensor 11 with the temperature measuring unit as shown in FIG. 7B is completed. The temperature sensor 11 is manufactured as described above.

As can be understood from the above process of manufacturing the temperature sensor 11, the second feature of the temperature sensor 11 is that the electrode 11-4B and the temperature measuring element 11-1 are electrically coupled to each other, but not bonded to each other by a conductive adhesive. Therefore, when the temperature sensor 11 is bonded to the hollow cylinder 14, the temperature sensor 11 can be adjusted in length and any damage to the temperature sensor 11 can be reduced.

Specifically, when the temperature sensor 11 with the temperature measuring unit, which is of a flat shape as shown in FIG. 7B, is bonded to the outer arcuate surface of the hollow cylinder 14, the temperature measuring unit tends to be arcuately curved along the outer arcuate surface of the hollow cylinder 14. It leads to develop large tensile stresses in the thin-film substrate 11-3B and the electrode 11-4B. Because the breaking strength of the thin-film substrate 11-3B is small, if the thin-film substrate 11-3B were bonded to the temperature measuring element 11-1 by a conductive adhesive, then the temperature measuring element 11-1 or the electrode 11-4B or their bonded surfaces would tend to be broken when the developed tensile stresses exceed the breaking strength.

According to the present invention, inasmuch as the temperature measuring element 11-1 and the electrode 11-4B are not bonded to each other by a conductive adhesive, the electrode 11-4B held in contact with the temperature measuring element 11-1 can be moved relatively thereto under developed tensile stresses. Consequently, the temperature measuring unit can be arcuately curved along the arcuate surface of the hollow cylinder 14. Since the developed tensile stresses are reduced, the temperature sensor 11 is prevented from being broken by its length adjusting function even when the temperature sensor 11 is bonded to the arcuate outer surface of the hollow cylinder 14.

As described above, one of the two electrodes held in contact with the temperature sensor 11 is brought into contact with the temperature sensor 11 by folding over the thin-film substrate 11-3. Thus, the temperature sensor 11 can easily and accurately be installed in position on the arcuately curved surface of the hollow cylinder 14.

However, because the electrode 11-4B and the temperature measuring element 11-1 of the temperature sensor 11 on the outer surface of the hollow cylinder 14 are not bonded to each other, their contacting surfaces may possibly be spaced from each other when the temperature sensor 11 is in use. If the contacting surfaces of the electrode 11-4B and the temperature measuring element 11-1 are spaced from each other, then the temperature sensor 11 will not function properly. To avoid this drawback, after the temperature sensor 11 is bonded to the outer surface of the hollow cylinder 14, the outer tube 16 is placed over the hollow cylinder 14 and then thermally shrunk to press the temperature sensor 11 in position, as described above with reference to FIGS. 5 and 6. As the electrode 11-4B and the temperature measuring element 11-1 are pressed against each other, though not bonded to each other by a conductive adhesive, the electrode 11-4B and the temperature measuring element 11-1 are prevented from being electrically disconnected from each other when the temperature sensor 11 is in use. The details shown in FIGS. 8A through 8D are by way of example only, and the positions of the electrodes and the conductors on the thin-film substrate can freely be changed insofar as the pressing electrode described above is obtained.

[Reflecting Surface (FIG. 2)]

The reflecting surface 21 of the laser beam irradiation portion 20 disposed in the insert portion 103 will be described below. The reflecting surface 21 constitutes part of the laser beam irradiation portion 20, and has a smooth surface for reflecting the laser beam emitted from the distal end of the optical fiber 12 through the laser beam irradiating window 17 to the target region T-1.

[Monorail Pipe (FIG. 2)]

As shown in FIG. 2, the monorail pipe 25 is a hollow pipe for passing a cleaning medium such as a cleaning liquid, a cleaning gas, or the like therethrough. The monorail pipe 25 allows the reciprocating movable member 23 to move therealong in the longitudinal direction of the insert portion 103, and also serves as a pipe for supplying a cleaning medium such as a cleaning liquid, a cleaning gas, or the like from a cleaning unit (not shown) to the front window 32 of the insert portion 103 when the front window 32 is dirtied.

The cleaning liquid may be a liquid such as sterilized water or sterilized physiological saline. The cleaning liquid is introduced under pressure from the cleaning unit (not shown) into the monorail pipe 25 to remove dirty deposits from the front window 32, and supplied through a cleaning liquid passage in the insert portion 103 to the front window 32 to remove dirty deposits on the front window 32.

The cleaning liquid may be replaced with a cleaning gas such as compressed air, a nitrogen gas, an oxygen gas, a carbon dioxide gas, or the like.

[Reciprocating Movable Member (FIG. 2)]

The reciprocating movable member 23 serves to change the direction of the applied laser beam depending on the irradiating position thereof when the reciprocating movable member 23 moves on the monorail pipe 25 in the directions indicated by the arrows, i.e., in the longitudinal directions of the applicator 110, e.g., from the position (a) to the position (b) to the position (c) to the position (b) to the position (a). Therefore, the direction of the applied laser beam and the irradiating position thereof can continuously be changed to control the laser beam to irradiate the target position at all times.

The reciprocating movable member 23 supports the laser beam irradiation portion 20 for reciprocating movement therewith. The reciprocating movable member 23 is positioned on one end of the laser beam irradiation portion 20, and the lugs 26 are positioned on the opposite end of the laser beam irradiation portion 20. The laser beam irradiation portion 20 is mounted on the reciprocating movable member 23 by the pivots 27 for free angular movement with respect to the reciprocating movable member 23 for thereby allowing the angle of the reflecting surface 21 to be changed with respect to the reciprocating movable member 23. The lugs 26 are fitted in the respective nonparallel grooves 42 that are defined in the inner surfaces of the walls 40, 41 disposed in the insert portion 103.

The reciprocating movable member 23 is coupled to the drive unit 150 (see FIG. 1), which is disposed on the proximal end of the applicator 110. When the reciprocating movable member 23 is slid on the monorail pipe 25 by the drive unit 150, the laser beam irradiation portion 20 is reciprocating moved in the longitudinal directions of the insert portion 103. When the laser beam irradiation portion 20 is axially moved by the reciprocating movable member 23 that travels on the monorail pipe 25, the laser beam irradiation portion 20 is caused by the nonparallel grooves 42 to change the angle of the reflecting surface 21.

[Direction of the Applied Laser Beam (FIG. 9)]

Figure 9:
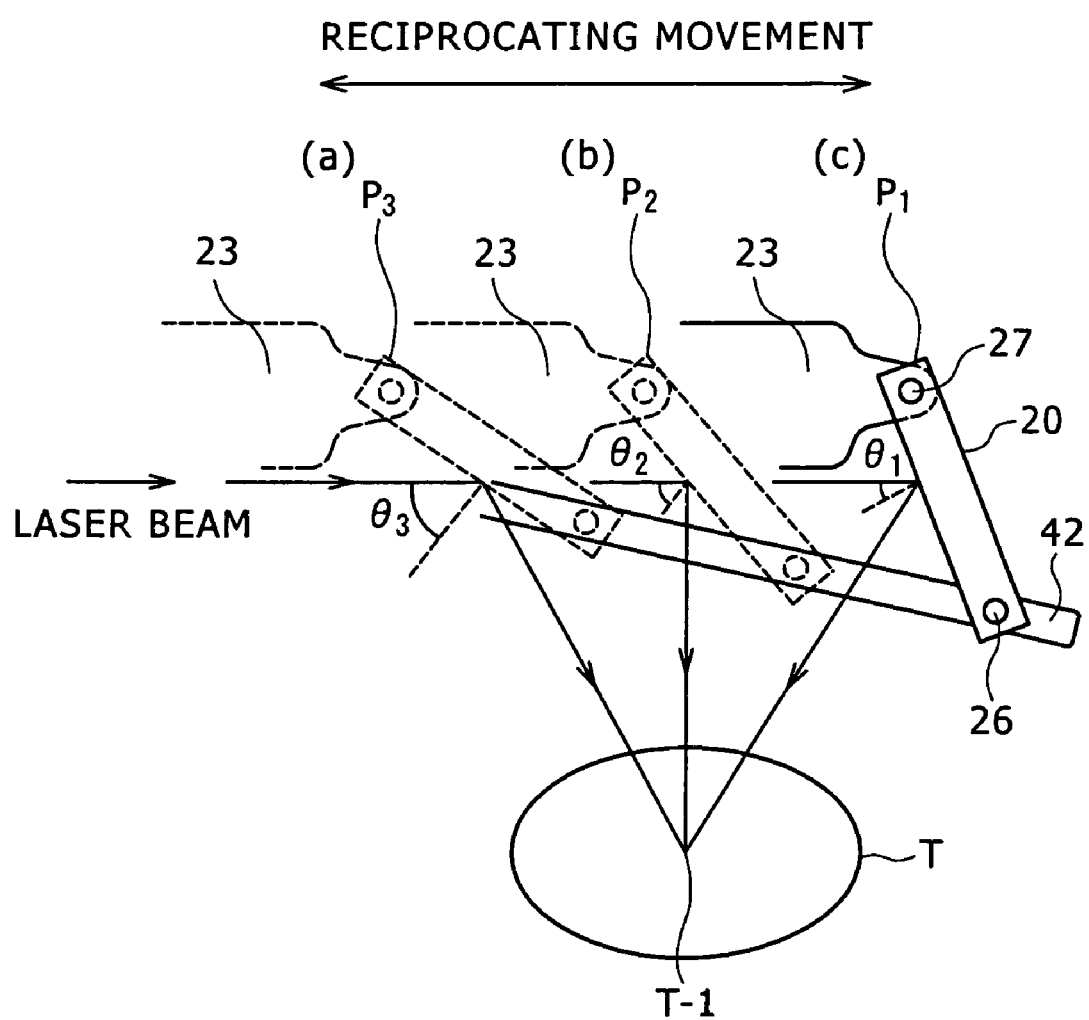
FIG. 9 is a view illustrative of the relationship between the movement of a reflecting surface and a living tissue region (target point) where a laser beam is concentrated.

FIG. 9 is illustrative of the relationship between the movement of the laser beam irradiation portion 20 and the direction of the applied laser beam reflected by the laser beam irradiation portion 20.

As shown in FIG. 9, the distance between the reciprocating movable member 23 and the nonparallel grooves 42 in the position P2 (the position (b)) is shorter than the distance between the reciprocating movable member 23 and the nonparallel grooves 42 in the position P1 (the position (c)). Therefore, when the reciprocating movable member 23 moves from the position P1 (the position (c)) to the position P2 (the position (b)), the lugs 26 of the laser beam irradiation portion 20 are lifted as they move along the nonparallel grooves 42. The angle of tilt of the laser beam irradiation portion 20 is adjusted. That is to say, the angle of tilt of the laser beam irradiation portion 20 with respect to the monorail pipe 25 is reduced. Similarly, when the reciprocating movable member 23 moves from the position P2 (the position (b)) to the position P3 (the position (a)), the angle of tilt of the laser beam irradiation portion 20 with respect to the monorail pipe 25 is further reduced.

The laser beam reflected by the laser beam irradiation portion 20 is applied to the target region T-1 (target point) of the prostate T at all times when the reciprocating movable member 23 is in the positions P1 through P3. Therefore, the laser beam continuously irradiates the target region T-1, and intermittently irradiates other tissue regions such as the surface layer of the body cavity U. The target region T-1 that is continuously irradiated with the laser beam generates a large amount of heat and reaches a desired high temperature, whereas the surface layer of the body cavity U, which is intermittently irradiated with the laser beam, generates a small amount of heat and is not heated to a high temperature. Consequently, only the target region T-1 and its surrounding regions are selectively heated by the laser beam for treatment with heat.

The laser beam irradiation portion 20 for reflecting the laser beam is reciprocating moved on and along the monorail pipe 25 in periodic cycles at a frequency ranging from 2 to 10 Hz, preferably 3 to 9 Hz, in the longitudinal direction of the insert portion 103 while changing its angle.

Figure 10:
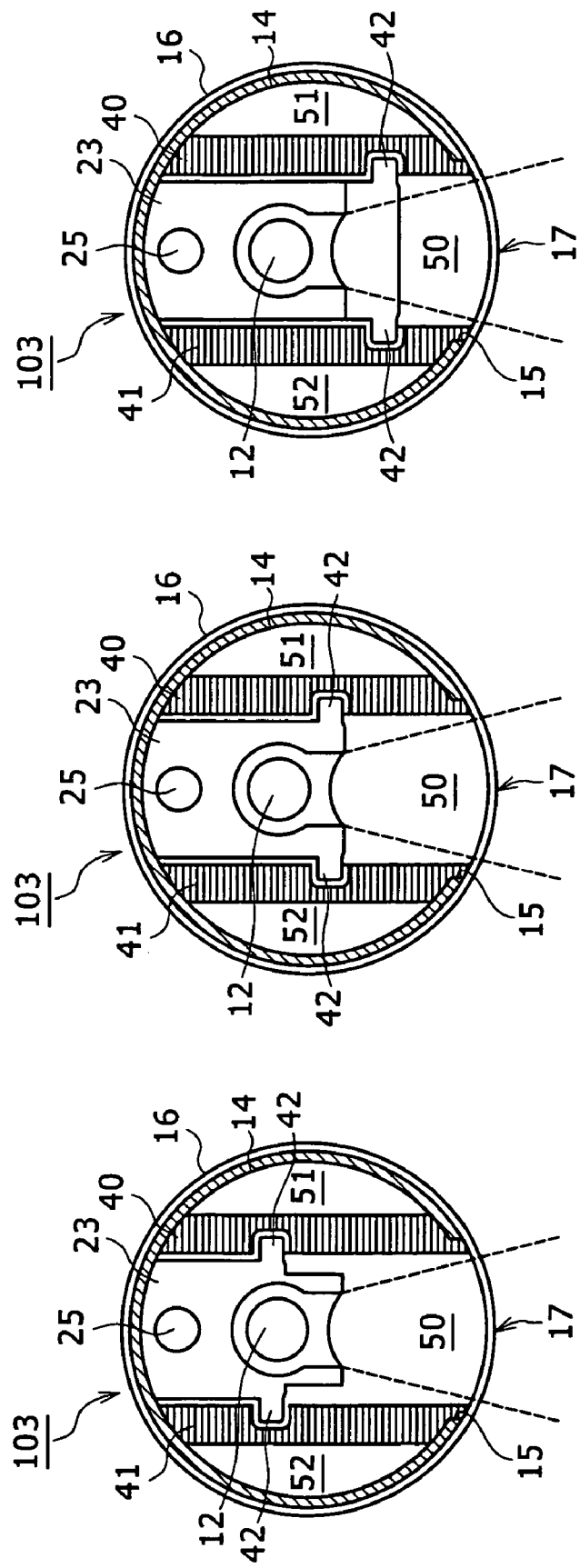
FIGS. 10A through 10C are transverse cross-sectional views showing the relationship between the positions of non-parallel grooves at different cross-sectional positions.

[Nonparallel Grooves (FIG. 10)]

Structural details of the nonparallel grooves 42 will be described below with reference to FIGS. 10A through 10C.

FIGS. 10A through 10C are transverse cross-sectional views of the insert portion 103 respectively at the positions (a), (b), and (c) in FIG. 2, showing the different vertical positions of the nonparallel grooves 42 defined in the walls 40, 41 at the respective positions (a), (b), and (c).

As shown in FIGS. 10A through 10C, the two laterally spaced walls 40, 41 are disposed in the insert portion 103. The monorail pipe 25 for delivering the cleaning medium therethrough, the optical fiber 12 for guiding the laser beam, and a coolant inlet lumen 50 for delivering the coolant to the distal end of the insert portion 103 are disposed between the walls 40, 41.

Coolant outlet lumens 51, 52 for returning the coolant from the distal end of the insert portion 103 to the coolant circulator 104 are disposed between the circumferential wall of the hollow cylinder 14 and the walls 40, 41.

The position of the nonparallel grooves 42 at the position in FIG. 10A is higher than the position of the nonparallel grooves 42 at the position in FIG. 10B. Therefore, the reflecting angle $\theta_3$ of the laser beam irradiation portion 20 for reflecting the laser beam at the position (a) in FIG. 9 is greater than the reflecting angle $\theta_2$ of the laser beam irradiation portion 20 for reflecting the laser beam at the position (b) in FIG. 9.

Likewise, the position of the nonparallel grooves 42 at the position in FIG. 10B is higher than the position of the nonparallel grooves 42 at the position in FIG. 10C. Therefore, the reflecting angle $\theta_2$ of the laser beam irradiation portion 20 for reflecting the laser beam at the position (b) in FIG. 9 is greater than the reflecting angle $\theta_1$ of the laser beam irradiation portion 20 for reflecting the laser beam at the position (c) in FIG. 9.

Consequently, the laser beam reflected by the laser beam irradiation portion 20 is concentrated on the target region T-1 at all times based on the different vertical positions of the nonparallel grooves 42.

[Temperature Control System (FIG. 11)]

A temperature control system of the medical energy irradiating apparatus will be described below.

Figure 11:
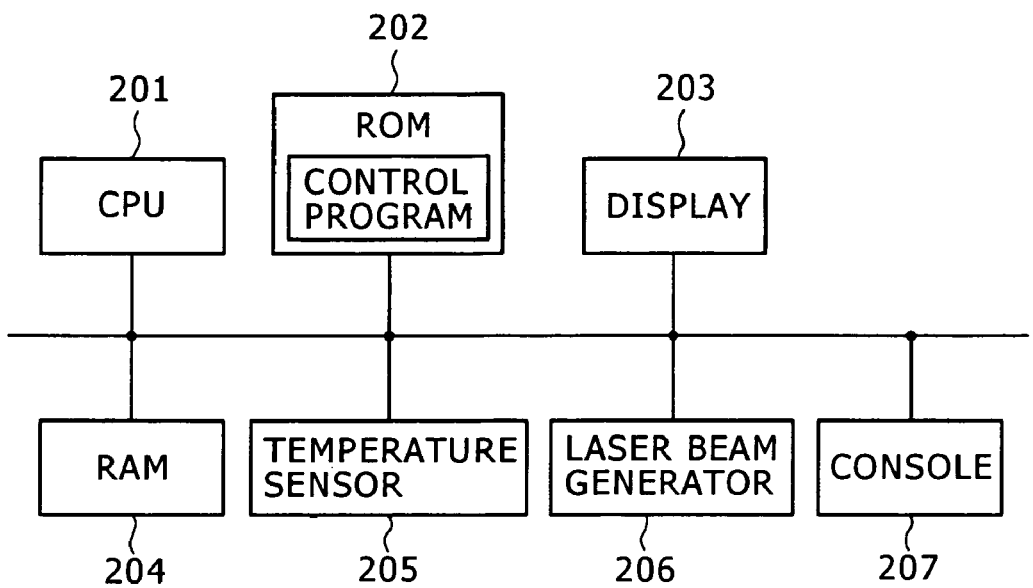
FIG. 11 is a block diagram of a control circuit of the medical energy irradiating apparatus.

FIG. 11 shows in block form a control circuit of the medical energy irradiating apparatus. As shown in FIG. 11, the control circuit includes a CPU 201, a ROM 202 for storing a control program that is executed by the CPU 201, a display 203, a RAM 204 for storing various data, a temperature sensor 205, a laser beam generator 206, and a console 207.

Operation of the control circuit will be described below. The console 207 includes a keyboard or the like. The user enters from the console 207 a signal for starting various processes for displaying a maximum surface temperature, displaying a deep region temperature, determining an incorrect irradiation timing, and controlling a laser beam output level. When the CPU 201 receives a command for executing the various processes, the CPU 201 operates according to the control program stored in the ROM 202 to receive measured values of the surface temperature from the temperature sensor 11 in the insert portion 103, store the measured values in the RAM 204, and control the laser beam generator 206 and the display 203 based on the measured values for displaying a maximum surface temperature, displaying a deep region temperature, determining an incorrect irradiation timing, and controlling a laser beam output level.

[Process of Estimating Maximum Cavity Wall Temperature (FIGS. 12 through 14)]

A process of estimating a maximum cavity wall temperature upon laser beam irradiation from measured values of the surface temperature, which are produced by the temperature sensor 11 in the insert portion 103 when the doctor treats an affected region with the medical energy irradiating apparatus 10, will be described below.

First, measuring conditions will be described below. The temperature sensor 11 is disposed at a circumferential end of the laser beam irradiating window 17 shown in FIG. 4 in its longitudinally central area, and measures a surface temperature Tu upon laser beam irradiation. A maximum cavity wall temperature Tmax upon laser beam irradiation is always observed at a central point A in the laser beam irradiating window 17 shown in FIG. 4. The maximum cavity wall temperature Tmax is measured by a temperature sensor, separate from the temperature sensor 11, positioned at the central point A. Tcool represents the temperature of the coolant for cooling the interior of the insert portion 103.

Figure 12:
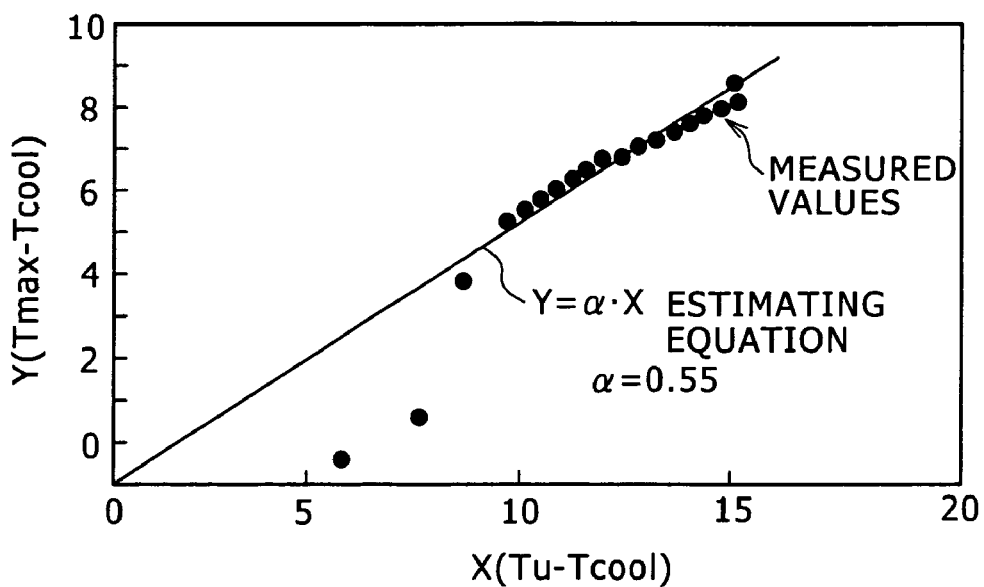
FIG. 12. is a diagram showing the correlation between measured values of the surface temperature and measured values of the maximum temperature of the lumen when a laser beam is applied.

FIG. 12 shows the correlation between measured values of the surface temperature and measured values of the maximum cavity wall temperature upon laser beam irradiation. In FIG. 12, the horizontal axis represents X =Tu−Tcool and the vertical axis Y=Tmax−Tcool. Solid dots in FIG. 12 show measured values. In FIG. 12, a linear curve Y=α·X represents an estimating equation determined by linearly approximating the measured values, where α=0.55. As it is understood from FIG. 12 that the surface temperature Tu and the maximum cavity wall temperature Tmax upon laser beam irradiation satisfy the following equation:

$$Tmax=Tcool+\alpha(Tu-Tcool) \qquad (1)$$

the maximum cavity wall temperature Tmax can be estimated from the surface temperature Tu upon laser beam irradiation according to the equation (1).

Figure 13:
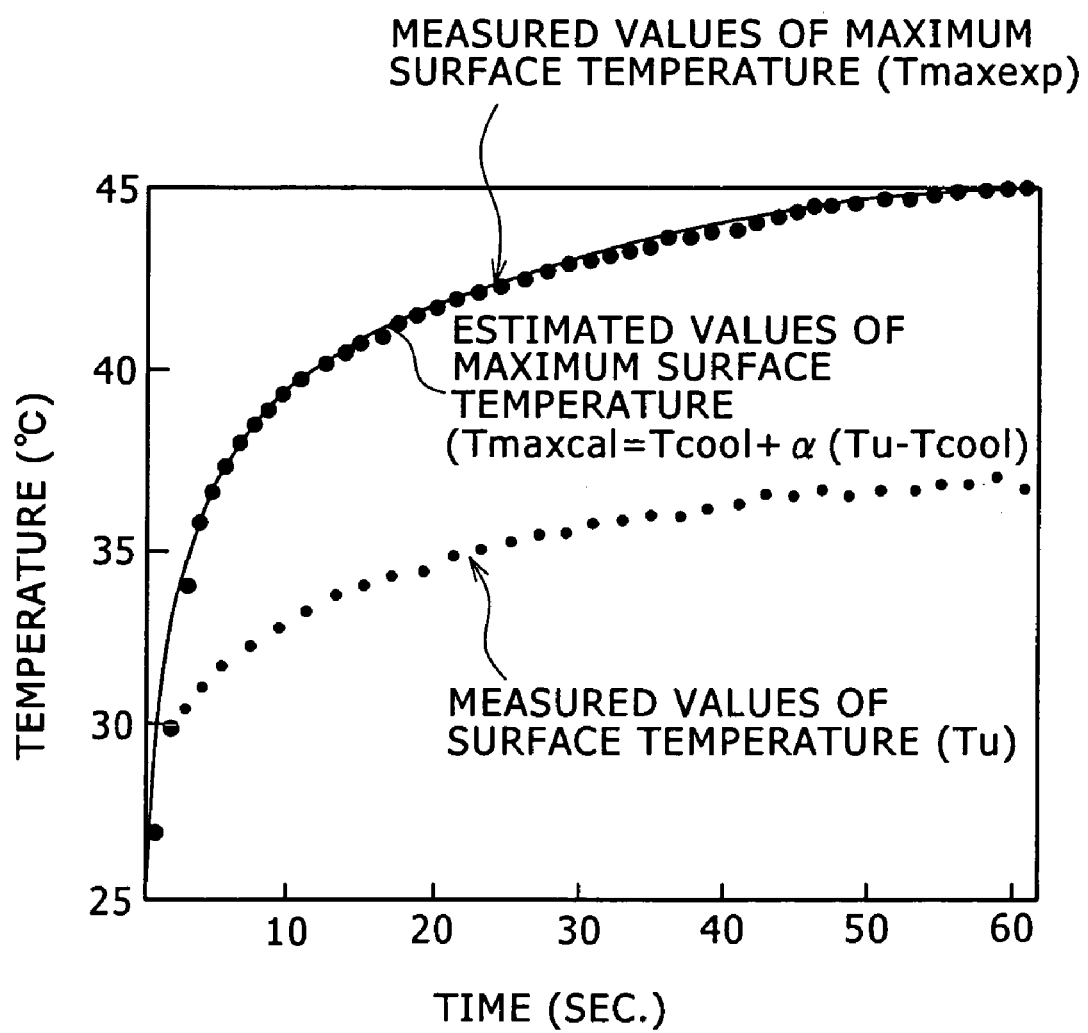
FIG. 13 is a diagram showing measured values of the surface temperature Tu when a laser beam is applied at desired times and estimated values, calculated according to an equation (1), of the maximum temperature of the lumen and measured values thereof.

FIG. 13 shows estimated values (Tmaxcal) of the maximum cavity wall temperature obtained from the surface temperature Tu upon laser beam irradiation according to the equation (1), and measured values (Tmaxexp) of the maximum cavity wall temperature. Since the measured and estimated values of the maximum cavity wall temperature at desired times agree with each other, the maximum cavity wall temperature Tmax can be estimated from the surface temperature Tu upon laser beam irradiation according to the equation (1).

Figure 14:
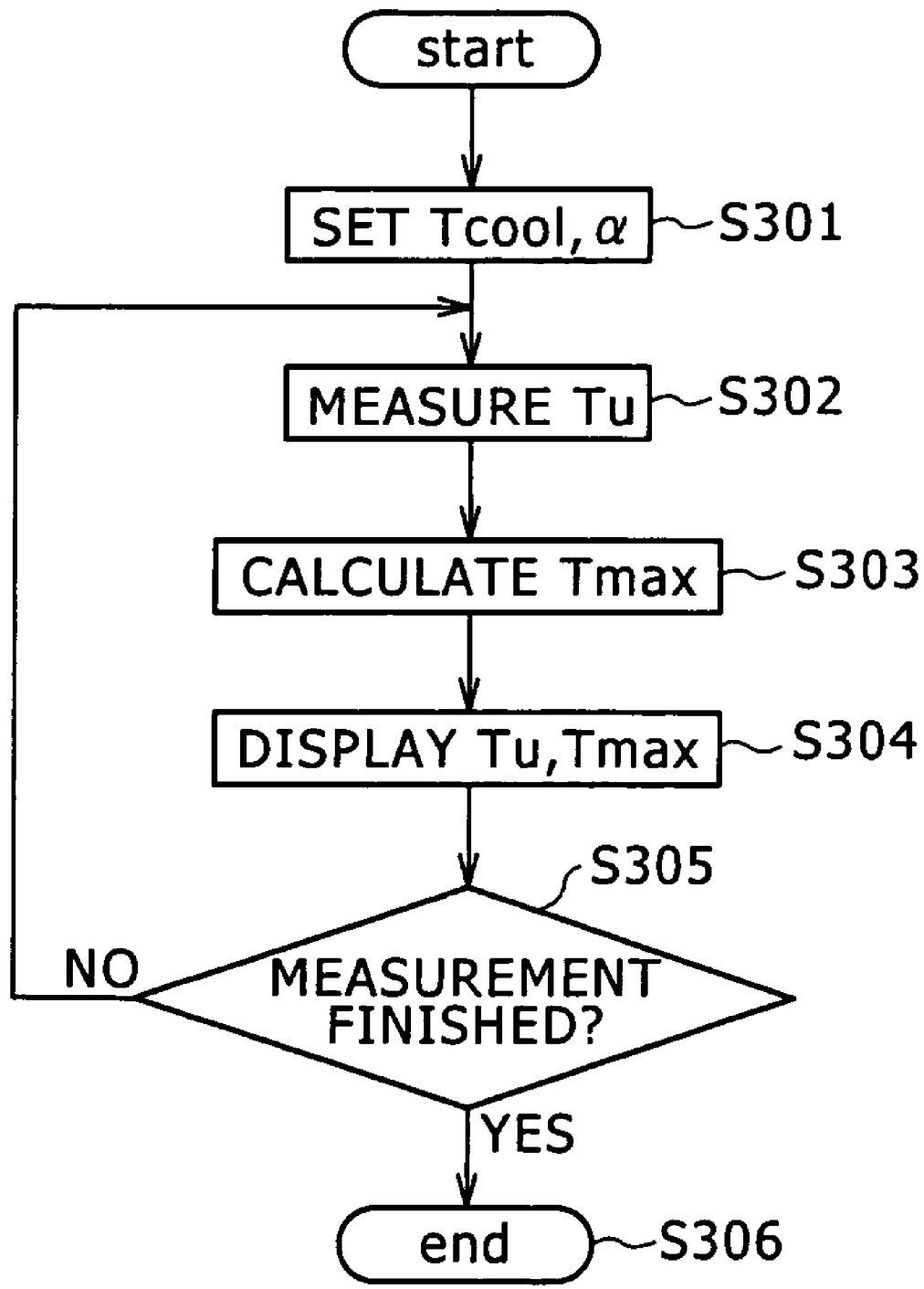
FIG. 14 is a flowchart of a process of calculating the maximum temperature Tmax of the lumen from the surface temperature Tu when a laser beam is applied.

Based on the above experimental results, a control program for calculating the maximum cavity wall temperature Tmax from the surface temperature Tu upon laser beam irradiation is produced and stored in the ROM 202. FIG. 14 shows a process carried out by the CPU 201 according to the control program. The process is started when the doctor enters an execution command and initial values for executing the control program from the console when the doctor treats an affected region with the medical energy irradiating apparatus.

In step S301, Tcool and α are set. In step S302, the surface temperature Tu is measured. In step S303, the maximum cavity wall temperature Tmax is calculated according to the equation (1). In step S304, the measured surface temperature Tu and the calculated maximum cavity wall temperature Tmax are displayed on the display. If a next measuring cycle is to be performed in step S305, then control goes back to step S302, and the above process is repeated. If the present measuring cycle is to be finished in step S305, then control goes to step S306, putting the process to an end.

[Process of Estimating Deep Region Temperature (FIGS. 15 and 16)]

A process of estimating a deep region temperature in a living body upon laser beam irradiation from measured values of the surface temperature, which are produced by the temperature sensor 11 in the insert portion 103 when the doctor treats an affected region with the medical energy irradiating apparatus 10, will be described below.

First, measuring conditions will be described below. The temperature sensor 11 is disposed at a circumferential end of the laser beam irradiating window 17 shown in FIG. 4 in its longitudinally central area, and measures a surface temperature Tu upon laser beam irradiation. The temperature sensor measures a deep region temperature Tp in a living body upon laser beam irradiation. The temperature sensor has thrusting into a living tissue to a depth of 1 cm directly below the surface of the living tissue that is held in contact with a central point A in the laser beam irradiating window 17 shown in FIG. 4. Tu0 represents an initial value of the temperature measured by the temperature sensor 11.

A process that is the same as the process described above with reference to FIG. 12 is carried out. As it is understood that the surface temperature Tu and the deep region temperature Tp upon laser beam irradiation satisfy the following equation:

$$Tp=Tu0+\beta(Tu-Tu0) \qquad (2)$$

the deep region temperature Tp can be estimated from the surface temperature Tu upon laser beam irradiation according to the equation (2).

Figure 15:
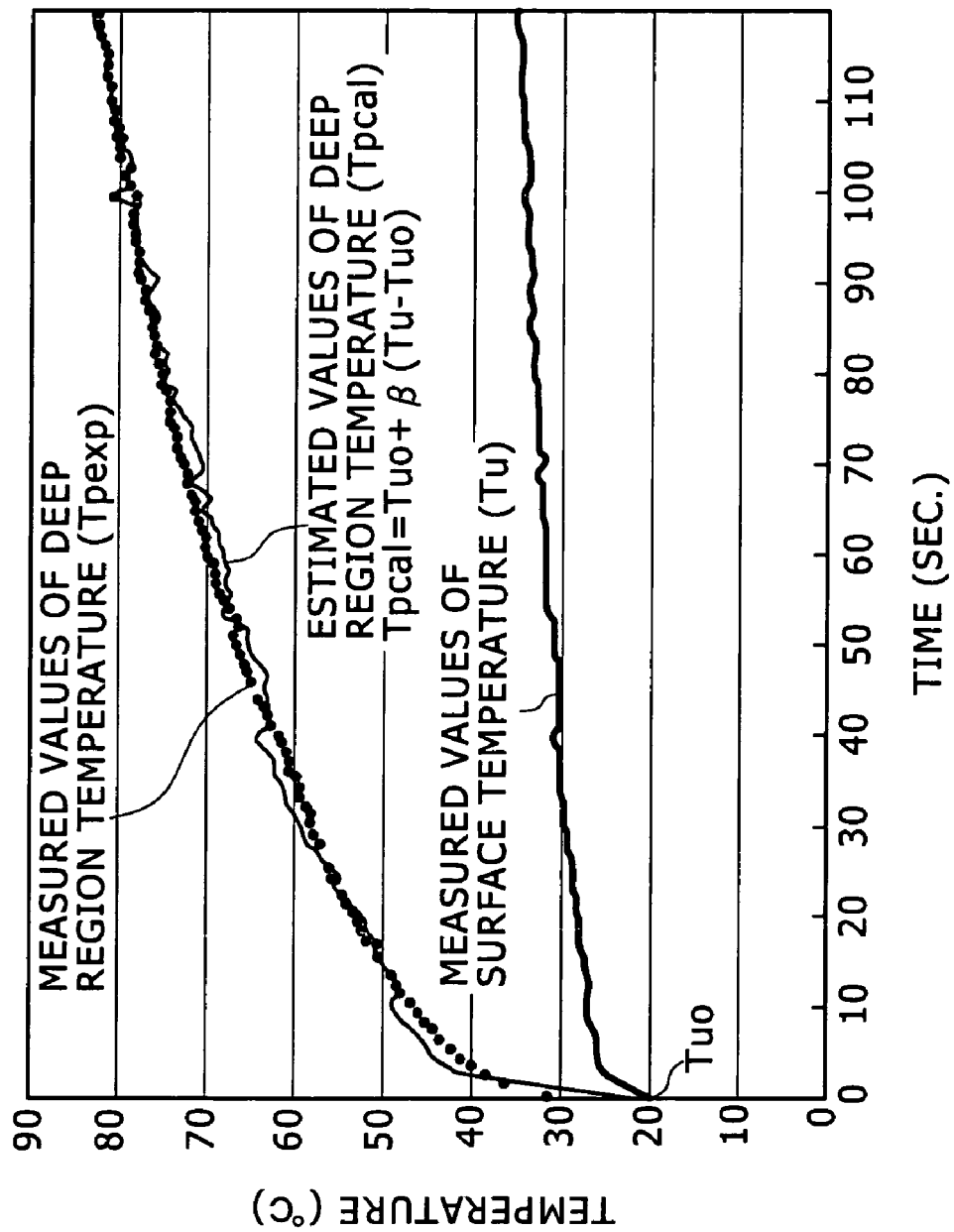
FIG. 15 is a diagram showing measured values of the surface temperature Tu when a laser beam is applied at desired times and estimated values, calculated according to an equation (2), of the temperature of a deep region in a living body and measured values thereof.

FIG. 15 shows estimated values (Tpcal) of the deep region temperature obtained from the surface temperature Tu upon laser beam irradiation according to the equation (2), and measured values (Tpexp) of the deep region temperature. Since the measured and estimated values of the deep region temperature at desired times agree with each other, the deep region temperature Tp can be estimated from the surface temperature Tu upon laser beam irradiation according to the equation (2).

Figure 16:
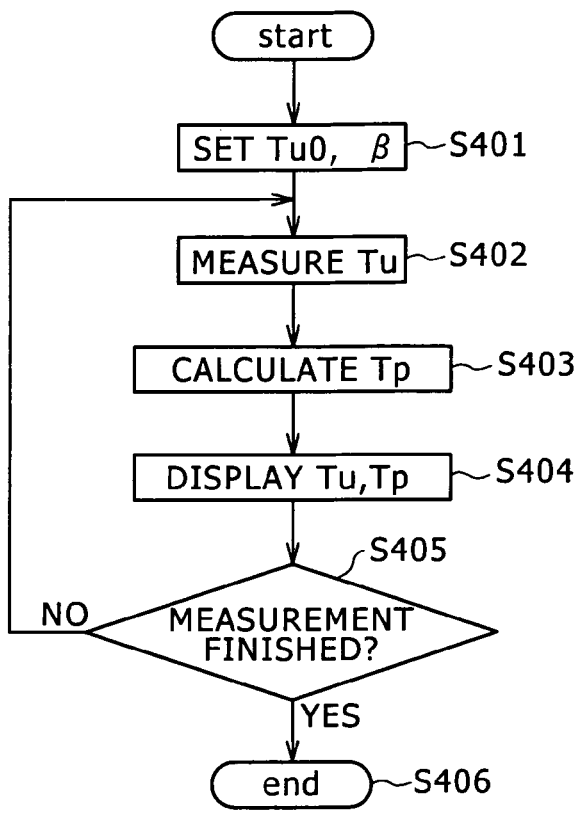
FIG. 16 is a flowchart of a process of calculating the temperature Tp of the deep region in the living body from the surface temperature Tu when a laser beam is applied.

Based on the above experimental results, a control program for calculating the deep region temperature Tp from the surface temperature Tu upon laser beam irradiation is produced and stored in the ROM 202. FIG. 16 shows a process carried out by the CPU 201 according to the control program. The process is started when the doctor enters an execution command and initial values for executing the control program from the console when the doctor treats an affected region with the medical energy irradiating apparatus.

In step S401, Tu0 and β are set. In step S402, the surface temperature Tu is measured. In step S403, the deep region temperature Tp is calculated according to the equation (2). In step S404, the measured surface temperature Tu and the calculated deep region temperature Tp are displayed on the display. If a next measuring cycle is to be performed in step S405, then control goes back to step S402, and the above process is repeated. If the present measuring cycle is to be finished in step S405, then control goes to step S406, putting the process to an end.

[Monitoring of Reciprocating Motion Timing (FIGS. 17 and 18)]

A process of monitoring irradiation timing upon laser beam irradiation from measured values of the surface temperature, which are produced by the temperature sensor 11 in the insert portion 103 when the doctor treats an affected region with the medical energy irradiating apparatus 10, will be described below.

First, measuring conditions will be described below. The temperature sensor 11 is disposed at a circumferential end of the laser beam irradiating window 17 shown in FIG. 4 in its longitudinally central area, and measures a surface temperature Tu upon laser beam irradiation. The temperature sensor 11 used has laser beam shield plates uncovered.

Figure 17:
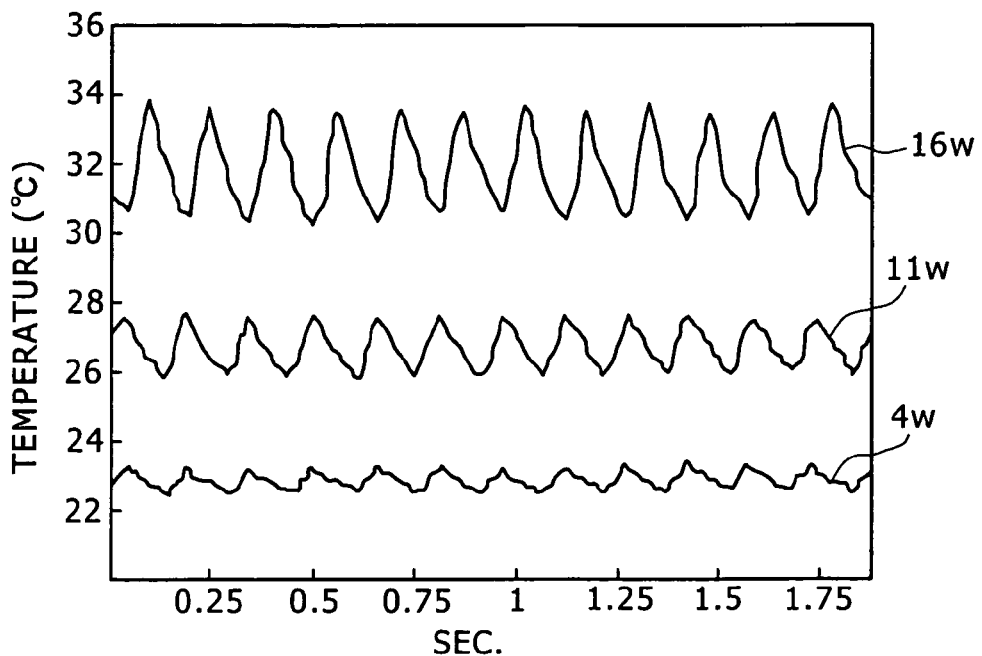
FIG. 17 is a diagram showing temperature changes caused in 2 seconds when laser beams are applied at output levels of 4, 11, and 16 W.

FIG. 17 shows temperature changes caused in 2 seconds when a laser beam is applied at output levels of 4, 11, and 16 W and the laser beam irradiation portion 20 is reciprocating moved at a frequency of 6 Hz. When a laser beam having an output level of 16 W is applied, the measured temperature values are in a range between a lowest temperature of 30° C. and a highest temperature of 34° C., and periodically vary six times per second. When laser beams having other output levels are applied, the measured temperature values also periodically vary six times per second. This indicates that the laser beam irradiation portion 20 is repeatedly reciprocating moved six times per second, applying the laser beam correctly to the target region. Therefore, it is possible to determine whether or not the laser beam irradiation portion 20 is operating correctly by measuring the number of periodical temperature changes per unit period of time. For example, under the above conditions, the irradiation timing is determined as being correct if six periodical temperature changes per second are detected, and is determined as being incorrect if more than six periodical temperature changes per second or less than six periodical temperature changes per second are detected.

[Detection of a Laser Beam Output Level]

The output level of a laser beam emitted from the laser beam generator can be measured from the range of temperature changes shown in FIG. 17. Specifically, the relationship between laser beam output levels and temperature changes may be stored in the ROM, and a laser beam output level may be calculated from a measured temperature change based on the stored relationship.

Figure 18:
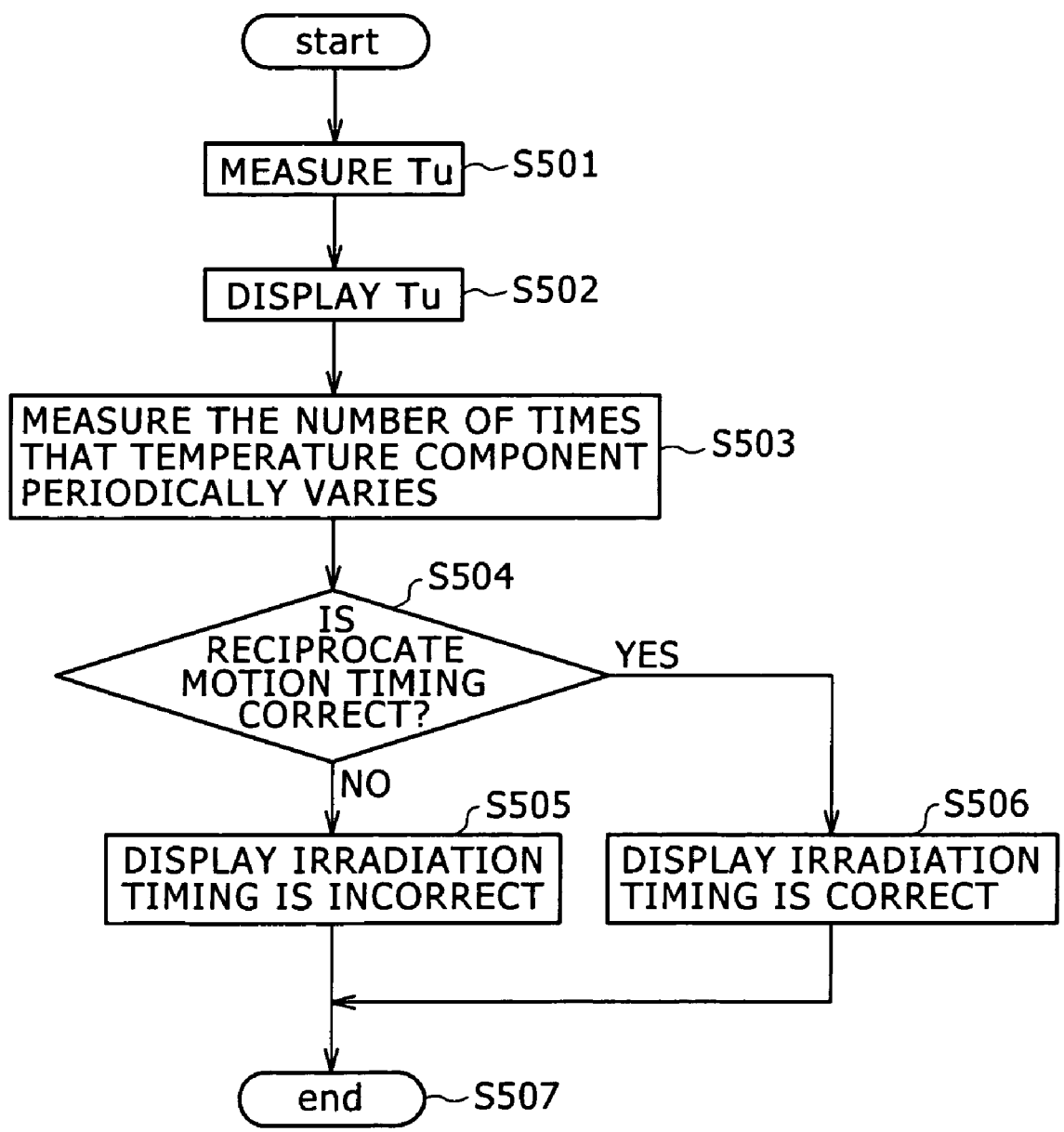
FIG. 18 is a flowchart of a process of determining whether irradiation timing is correct or incorrect from the surface temperature Tu when a laser beam is applied.

Based on the above experimental results, a control program for determining whether the irradiation timing is correct or not from the surface temperature Tu upon laser beam irradiation is produced and stored in the ROM 202. FIG. 18 shows a process carried out by the CPU 201 according to the control program. The process is started when the doctor enters an execution command and initial values for executing the control program from the console when the doctor treats an affected region with the medical energy irradiating apparatus.

In step S501, the surface temperature Tu is measured for a certain period of time. In step S502, the measured surface temperature Tu is displayed. In step S503, the number of periodic temperature changes is measured in the above period of time from the measured values of the surface temperature Tu, and it is checked whether or not the measured number of periodic temperature changes agrees with a preset number of periodic temperature changes. If the measured number of periodic temperature changes agrees with the preset number of periodic temperature changes, then control goes to step S506 in which correct reciprocating motion timing is displayed. Then, control goes to step S507 to put the process to an end. If the measured number of periodic temperature changes does not agree with the preset number of periodic temperature changes, then control goes to step S505 in which incorrect reciprocating motion timing is displayed. Then, control goes to step S507 to put the process to an end.

[Control of a Laser Beam Output Level (FIGS. 19 and 20)]

A process of controlling a laser beam output level upon laser beam irradiation based on measured values of the surface temperature, which are produced by the temperature sensor 11 in the insert portion 103 when the doctor treats an affected region with the medical energy irradiating apparatus 10, will be described below.

Figure 19:
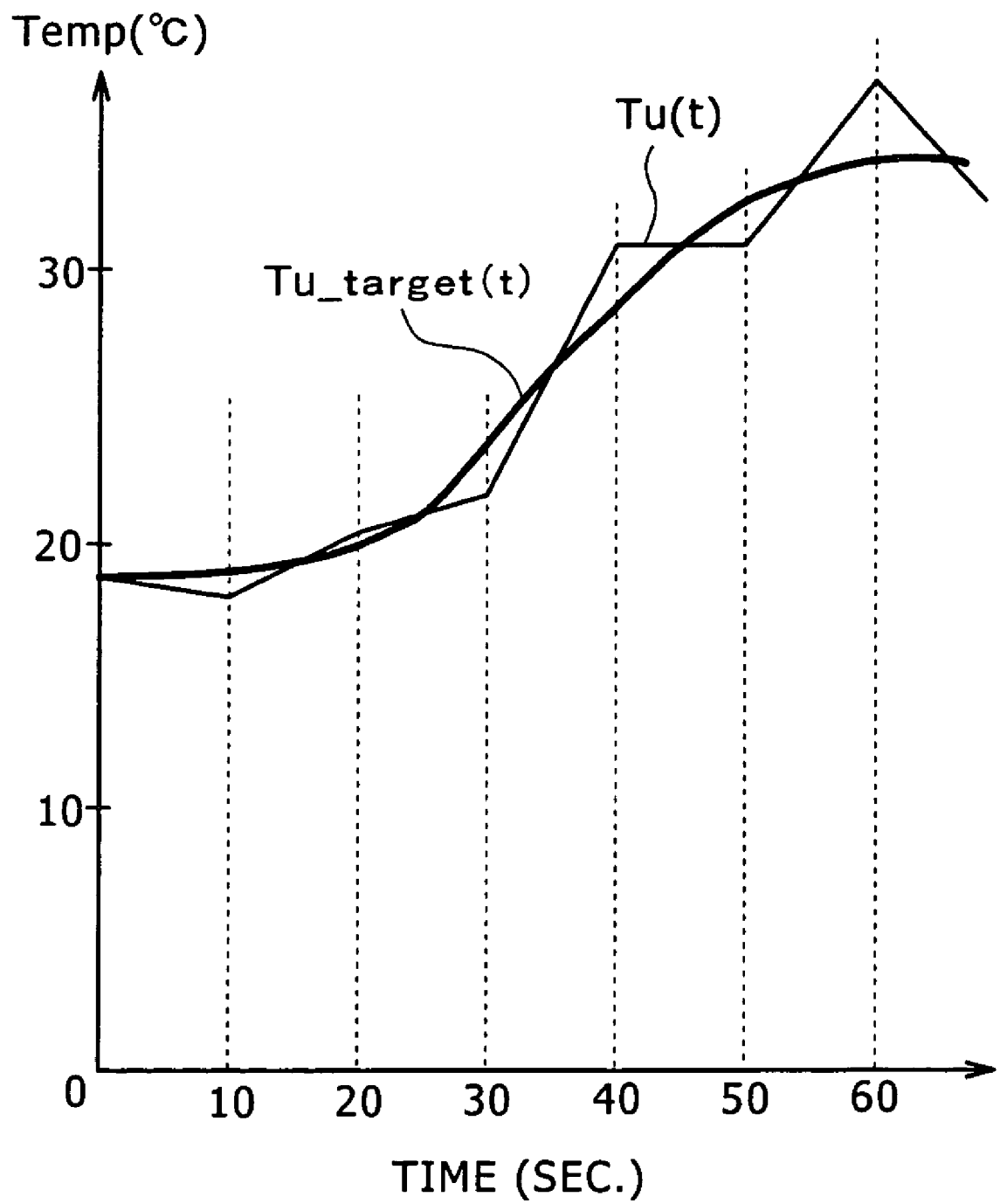
FIG. 19 is a diagram showing a temperature rise pattern Tutarget(t) of the surface temperature when a laser beam is applied and measured values of the surface temperature Tu(t)
Figure 20:
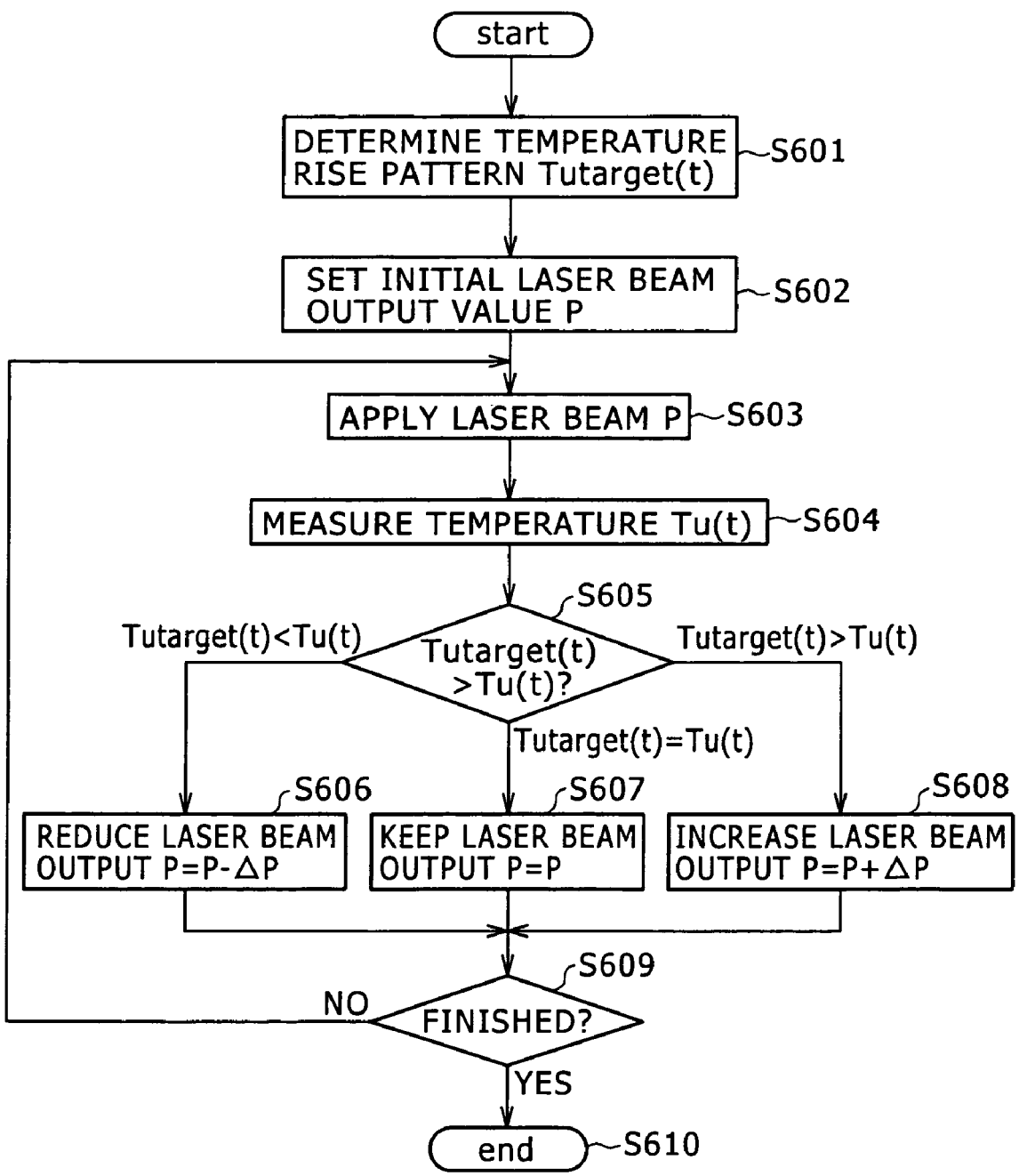
FIG. 20 is a flowchart of a process of controlling a laser beam output level from the surface temperature Tu when a laser beam is applied.

First, measuring conditions will be described below. The temperature sensor 11 is disposed at a circumferential end of the laser beam irradiating window 17 shown in FIG. 4 in its longitudinally central area, and measures a surface temperature Tu upon laser beam irradiation. FIG. 19 shows a preset temperature rise pattern Tutarget(t) of the surface temperature upon laser beam irradiation and measured values of the surface temperature Tu. A living tissue is heated according to the preset temperature rise pattern. It is necessary to change the laser beam output level upon laser beam irradiation from time to time. The laser beam output level is controlled by the CPU 201, which controls the laser beam generator 206, according to a predetermined control program based on the measured values of the surface temperature Tu. FIG. 20 shows a process carried out by the CPU 201 according to the control program. The process is started when the doctor enters an execution command and initial values for executing the control program from the console when the doctor treats an affected region with the medical energy irradiating apparatus.

In step S601, a temperature rise pattern Tutarget(t) of the surface temperature upon laser beam irradiation is determined. Specifically, the doctor selects a desired one of a plurality of preset temperature rise patterns, and the CPU 201 determines the temperature rise pattern based on a selection signal entered by the doctor. In step S602, an initial laser beam output level is set. In step S603, the target region is irradiated with a laser beam having the initial laser beam output level. In step S604, the surface temperature Tu(t) upon laser beam irradiation is measured. In step S605, the measured surface temperature Tu(t) is compared with the temperature rise pattern Tutarget(t). If Tutarget(t)<Tu(t) in step S605, then control goes to step S606 in which the laser beam output level P is changed to P−ΔP, after which control goes to step S609. If Tutarget(t)=Tu(t) in step S605, then control goes to step S607 in which the laser beam output level P is not changed, but maintained, after which control goes to step S609. If Tutarget(t)>Tu(t) in step S605, then control goes to step S608 in which the laser beam output level P is changed to P+ΔP, after which control goes to step S609. If a next output level controlling cycle is to be performed in step S609, then control goes back to step S603, and the above process is repeated. If the present output level controlling cycle is to be finished in step S609, then control goes to step S610, putting the process to an end.

[Another Embodiment (FIG. 21)]

Figure 21:
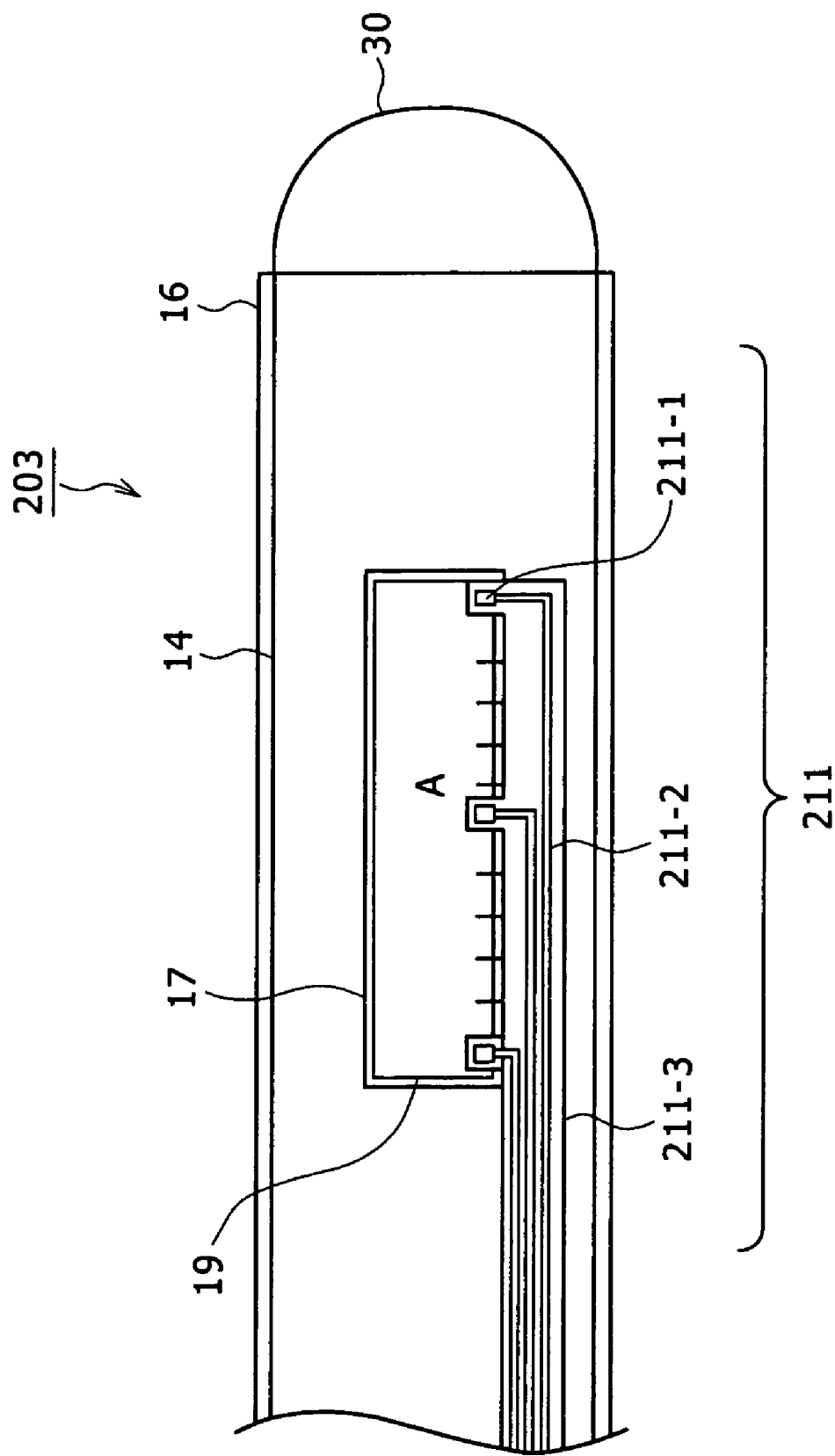
FIG. 21 is an elevational view of three independent temperature sensors disposed on one thin-film substrate.

In the above embodiment, the single temperature sensor 11 is disposed in the insert portion 103 as shown in FIG. 4. However, a plurality of temperature sensors may be disposed on the insert. FIG. 21 shows three independent temperature sensors disposed on one thin-film substrate. The temperature sensors shown in FIG. 21 can be manufactured according to a process based on the process shown in FIGS. 8A through 8D. Therefore, the process of manufacturing the temperature sensors shown in FIG. 21 will not be described in detail below. The plural temperature sensors shown in FIG. 21 make it possible to measure more accurately temperature changes in a living tissue as it is treated with heat.

The medical energy irradiating apparatus according to the present invention should preferably be used to treat a prostate with heat to cure a prostatic disease such as a prostatic hypertrophy, a prostatic cancer, or the like while reducing damage to a correct living tissue, such as the urethra, the rectum, or the like, that is positioned closely to the prostate.

As described above, the temperature measuring unit of the temperature sensor according to the present invention has the electrodes disposed on the upper and lower surfaces of the temperature measuring element, the thin-film substrates disposed on the upper and lower surfaces of the electrodes, and the laser beam shield plates disposed on the upper and lower surfaces of the thin-film substrates. The electrode 11-4A is bonded to the temperature measuring element by the conductive adhesive, and the electrode 11-4B is not bonded to the temperature measuring element by the conductive adhesive. When the temperature sensor is bonded to the hollow cylinder of the insert, the temperature measuring unit is curved along the surface of the hollow cylinder, tending to develop tensile stresses in the electrode 11-4B. At this time, the electrode 11-4B, which is not bonded to the temperature measuring element, is positionally displaced depending on the developed tensile stresses, allowing the temperature sensor to be adjusted in length. Consequently, the temperature sensor is prevented from being broken or damaged. Therefore, the medical energy irradiating apparatus according to the present invention is capable of accurately measuring the temperature of a living tissue as it is treated with heat, though the medical energy irradiating apparatus is simple in structure and inexpensive to manufacture. Therefore, the doctor who operates the medical energy irradiating apparatus can correctly monitor the temperature of the living tissue as it is treated with heat to cure a prostatic hypertrophy, for example, and hence can treat the living tissue with greater safety.

While preferred embodiments of the invention have been described using specific terms, such description is for illustrative purposes only, and it is to be understood that changes and variations may be made without departing from the spirit of scope of the following claims.

What is claimed is:

1. A medical energy irradiating apparatus comprising:
   an insert portion for being inserted into a living body;
   a temperature sensor disposed on said insert portion; and
   an energy irradiator for applying an energy to a living tissue of the living body;
   wherein said temperature sensor comprises:
   a single flexible thin-film substrate;
   at least first and second conductors disposed on said thin-film substrate;
   substantially plate-like first and second electrodes disposed on said thin-film substrate and electrically coupled respectively to said first and second conductors; and
   a substantially plate-like temperature measuring element;
   said first and second electrodes being electrically coupled to said temperature measuring element
   wherein said temperature measuring element has a first surface disposed on said first electrode, said first electrode being fixed and electrically coupled to said temperature measuring element, and wherein said temperature measuring element has a second surface opposite to said first surface said second electrode being disposed on said second surface, said second electrode being electrically coupled to said temperature measuring element without being fixed to said temperature measuring element.

2. The medical energy irradiating apparatus according to claim 1, wherein said single flexible thin-film substrate is curved to dispose said second electrode on said second surface opposite to said first surface of said temperature measuring element.

3. The medical energy irradiating apparatus according to claim 1, wherein said thin-film substrate is disposed along a longitudinal direction on an outer surface of said insert.

4. The medical energy irradiating apparatus according to claim 1, further comprising:
   a covering tube covering a portion of an outer surface of said insert and thermally shrunk over said insert and said temperature sensor to press said temperature measuring element and said second electrode against each other.

5. The medical energy irradiating apparatus according to claim 1, wherein said temperature sensor further comprises:
   a thin metal film shielding said temperature measuring element against light.

6. The medical energy irradiating apparatus according to claim 5, wherein said thin metal film is disposed on said thin-film substrate, and said thin-film substrate with said metal film disposed thereon is folded to cover said temperature measuring element.

7. The medical energy irradiating apparatus according to claim 1, further comprising:
   an energy irradiating window for applying an energy therethrough to a living tissue of the living body;
   said temperature sensor being disposed on said energy irradiating window.

8. The medical energy irradiating apparatus according to claim 7, wherein said insert portion comprises a hollow cylinder, said hollow cylinder having an opening defined in a side wall thereof and serving as said energy irradiating window.

9. The medical energy irradiating apparatus according to claim 8, further comprising: an optically transparent synthetic resin film applied to said hollow cylinder in covering relation to said opening.

10. The medical energy irradiating apparatus according to claim 9, wherein said optically transparent synthetic resin film has scale.

11. The medical energy irradiating apparatus according to claim 9, further comprising:
    at least an outer tube covering said opening.

12. The medical energy irradiating apparatus according to claim 1, wherein said thin-film substrate has depth markers for the user to read a length by which said insert is inserted into the living body.

13. The medical energy irradiating apparatus according to claim 1, further comprising:
    maximum surface temperature estimating means for estimating a maximum temperature of a surface of the living tissue, which is irradiated with said energy, based on a temperature measured by said temperature sensor.

14. The medical energy irradiating apparatus according to claim 1, further comprising:
    deep region temperature estimating means for estimating a deep region temperature in the living tissue, which is irradiated with said energy, based on a temperature measured by said temperature sensor.

15. The medical energy irradiating apparatus according to claim 1, further comprising:
    control means for controlling the energy applied to said living tissue based on a temperature measured by said temperature sensor.

16. The medical energy irradiating apparatus according to claim 1, wherein said energy comprises a laser beam.

17. The medical energy irradiating apparatus according to claim 16, further comprising:
    irradiating means disposed in said insert and having a reflecting surface for reflecting said laser beam through an energy irradiating window to the living tissue;
    moving means for reciprocating moving said irradiating means in a longitudinal direction of said insert;
    angle changing means for changing an angle through which said energy is applied to the living tissue by said irradiating means; and
    decision means for determining whether said irradiating means is correctly controlled to move reciprocating by said moving means based on a temperature measured by said temperature sensor.

18. The medical energy irradiating apparatus according to claim 1, further comprising:
    a plurality of the temperature sensors disposed in respective different positions on an outer surface of said insert.

* * * * *